(12) United States Patent
Fukushima

(10) Patent No.: US 10,955,656 B2
(45) Date of Patent: Mar. 23, 2021

(54) IMAGE-ACQUISITION APPARATUS

(71) Applicant: OLYMPUS CORPORATION, Hachioji (JP)

(72) Inventor: Ikutoshi Fukushima, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 612 days.

(21) Appl. No.: 15/832,090

(22) Filed: Dec. 5, 2017

(65) Prior Publication Data

US 2018/0095262 A1 Apr. 5, 2018

Related U.S. Application Data

(63) Continuation of application No. PCT/JP2015/071707, filed on Jul. 30, 2015.

(51) Int. Cl.
*G02B 23/24* (2006.01)
*A61B 1/00* (2006.01)
(Continued)

(52) U.S. Cl.
CPC .......... *G02B 23/2415* (2013.01); *A61B 1/00* (2013.01); *A61B 1/00096* (2013.01);
(Continued)

(58) Field of Classification Search
CPC .......... G02B 23/2415; G02B 23/2438; G02B 23/26; G02B 23/24; G02B 23/2407;
(Continued)

(56) References Cited

U.S. PATENT DOCUMENTS 5,496,261 A 3/1996 Sander
5,673,147 A 9/1997 McKinley
(Continued)

FOREIGN PATENT DOCUMENTS

JP 06331937 A 12/1994
JP 07059723 A 3/1995
(Continued)

OTHER PUBLICATIONS

International Search Report (ISR) and Written Opinion dated Oct. 6, 2015 issued in International Application No. PCT/JP2015/071707.

*Primary Examiner* — Stephone B Allen
*Assistant Examiner* — Adam W Booher
(74) *Attorney, Agent, or Firm* — Holtz, Holtz & Volek PC

(57) ABSTRACT

An image-acquisition apparatus is provided with: an imaging optical system; and an image-acquisition device that acquires parallax images, wherein the imaging optical system is provided with a first negative lens group, a first positive lens group, and a second positive lens group, wherein the first positive lens group and the first negative lens group are disposed along a common center axis, wherein the second positive lens group is provided with two positive lens groups that are disposed next to each other in a parallax direction on either side of the common center axis and that individually have center axes, wherein two aperture stops having openings, wherein the first positive lens group has only one moving lens group that is moved, and wherein all of remaining lens components in the imaging optical system, excluding the moving lens group, remain still.

5 Claims, 24 Drawing Sheets

(51) Int. Cl.
*G02B 23/26* (2006.01)
*G03B 35/10* (2006.01)

(52) U.S. Cl.
CPC ...... *A61B 1/00193* (2013.01); *G02B 23/2438* (2013.01); *G02B 23/26* (2013.01); *G03B 35/10* (2013.01)

(58) Field of Classification Search
CPC .. G02B 23/243; G02B 23/2446; G02B 15/14; G02B 30/00; G02B 30/10; G02B 30/20; G02B 30/22; A61B 1/00; A61B 1/00096; A61B 1/00193; G03B 35/10
See application file for complete search history.

(56) References Cited

U.S. PATENT DOCUMENTS

| | | | |
|---|---|---|---|
| 6,632,172 | B1 | 10/2003 | Igarashi |
| 8,144,394 | B2 | 3/2012 | Uzawa |
| 2003/0125608 | A1 | 7/2003 | Igarashi |
| 2017/0293129 | A1* | 10/2017 | Hatakeyama ........ G02B 21/025 |

FOREIGN PATENT DOCUMENTS

| | | | |
|---|---|---|---|
| JP | 11503844 | A | 3/1999 |
| JP | 2001147382 | A | 5/2001 |
| JP | 2009265221 | A | 11/2009 |
| JP | 2014140593 | A | 8/2014 |
| JP | 2014174390 | A | 9/2014 |
| WO | 9633436 | A1 | 10/1996 |

* cited by examiner

FIG. 5
FAR POINT
(a) IMAGE HEIGHT 0.4
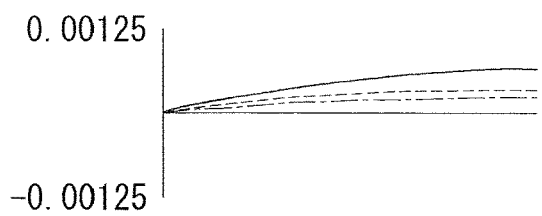
(b) IMAGE HEIGHT 0.3
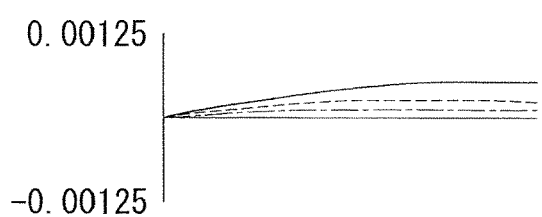
(c) IMAGE HEIGHT 0.2
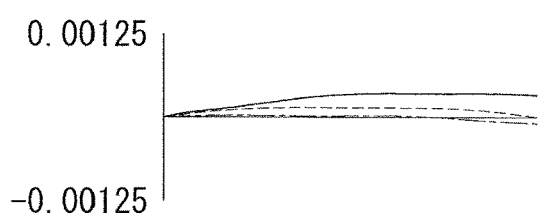
(d) IMAGE HEIGHT 0.1
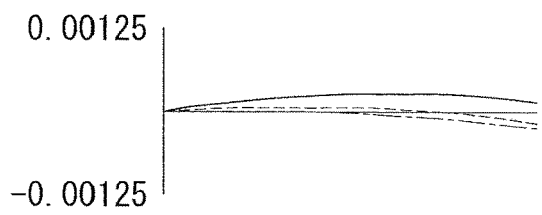
(e) IMAGE HEIGHT 0.0
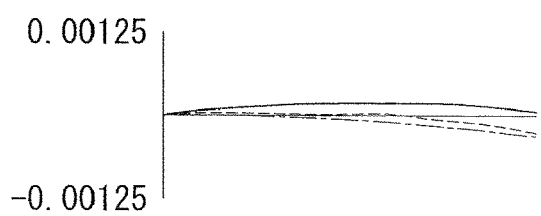
(f) IMAGE HEIGHT -0.2
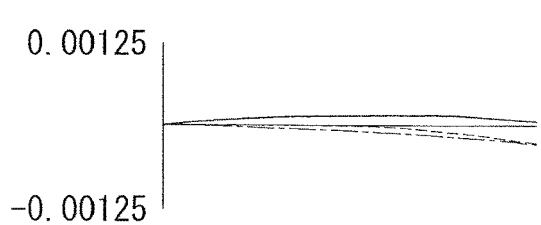
(g) IMAGE HEIGHT -0.4
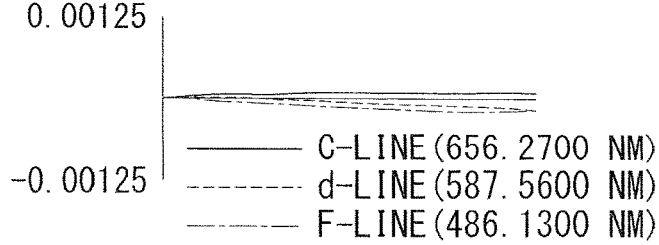
—— C-LINE (656.2700 NM)
------ d-LINE (587.5600 NM)
—·— F-LINE (486.1300 NM)

FIG. 6
NEAR POINT
(a) IMAGE HEIGHT 0.4
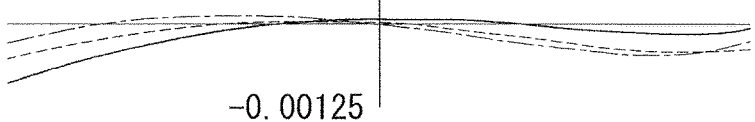
(b) IMAGE HEIGHT 0.3
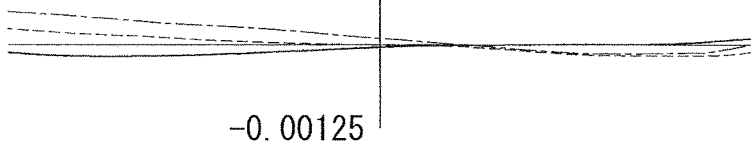
(c) IMAGE HEIGHT 0.2
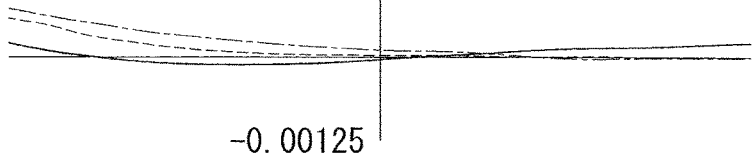
(d) IMAGE HEIGHT 0.1
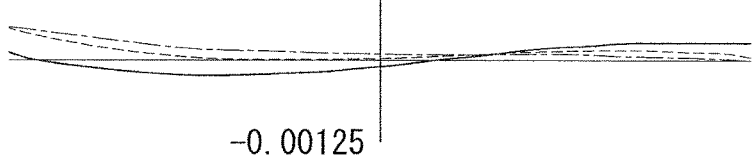
(e) IMAGE HEIGHT 0.0
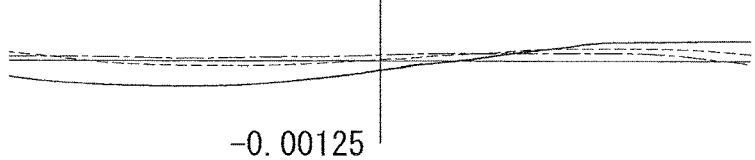
(f) IMAGE HEIGHT -0.2
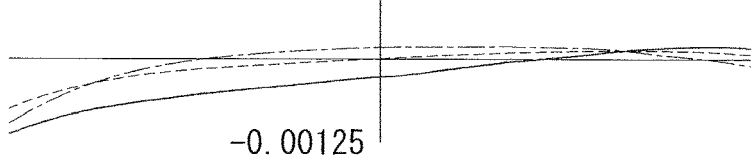
(g) IMAGE HEIGHT -0.4
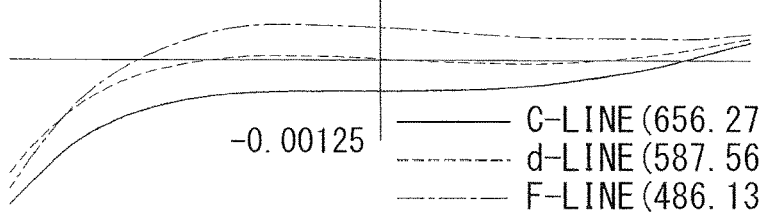
— C-LINE (656.2700 NM)
----- d-LINE (587.5600 NM)
-·-·- F-LINE (486.1300 NM)

FIG. 7

NEAR POINT
(a) IMAGE HEIGHT 0.4
(b) IMAGE HEIGHT 0.3
(c) IMAGE HEIGHT 0.2
(d) IMAGE HEIGHT 0.1
(e) IMAGE HEIGHT 0.0
(f) IMAGE HEIGHT -0.2
(g) IMAGE HEIGHT -0.4

——— C-LINE (656.2700 NM)
- - - - d-LINE (587.5600 NM)
—·—·— F-LINE (486.1300 NM)

FIG. 12
FAR POINT
(a) IMAGE HEIGHT 0.4    0.00125
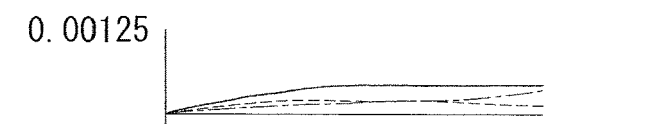
                        -0.00125
(b) IMAGE HEIGHT 0.3    0.00125
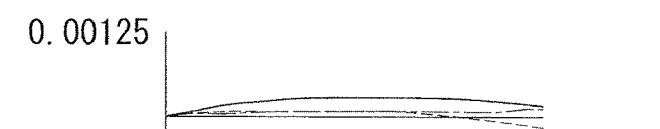
                        -0.00125
(c) IMAGE HEIGHT 0.2    0.00125
                        -0.00125
(d) IMAGE HEIGHT 0.1    0.00125
                        -0.00125
(e) IMAGE HEIGHT 0.0    0.00125
                        -0.00125
(f) IMAGE HEIGHT -0.2   0.00125
                        -0.00125
(g) IMAGE HEIGHT -0.4   0.00125
                        -0.00125
——— C-LINE (656.2700 NM)
- - - - d-LINE (587.5600 NM)
— - — F-LINE (486.1300 NM)

FIG. 19
FAR POINT
(a) IMAGE HEIGHT 0.4
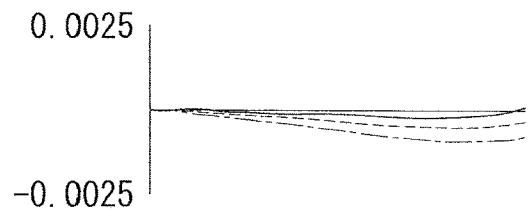
(b) IMAGE HEIGHT 0.3
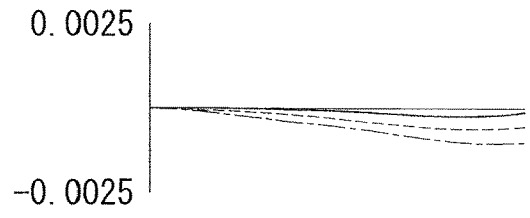
(c) IMAGE HEIGHT 0.2
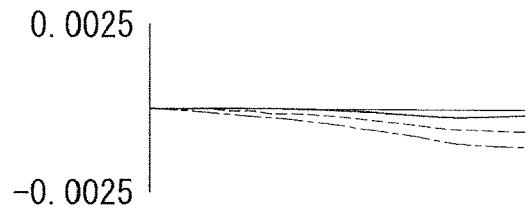
(d) IMAGE HEIGHT 0.1
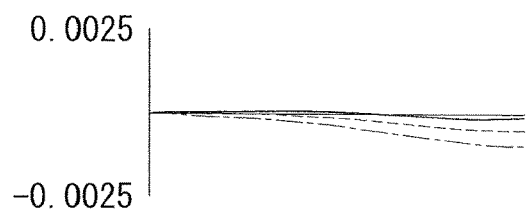
(e) IMAGE HEIGHT 0.0
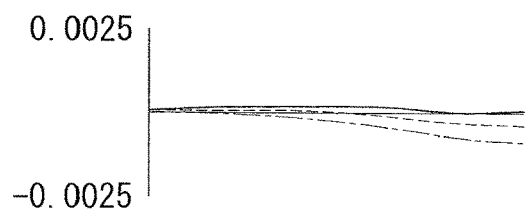
(f) IMAGE HEIGHT −0.2
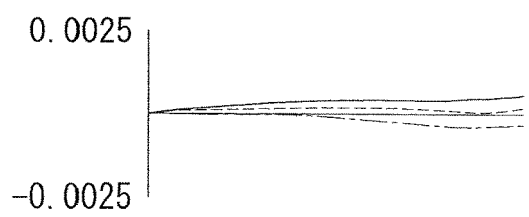
(g) IMAGE HEIGHT −0.4
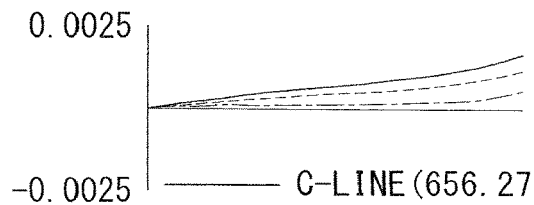
―――― C-LINE (656.2700 NM)
------ d-LINE (587.5600 NM)
―・― F-LINE (486.1300 NM)

FIG. 20

NEAR POINT (a) IMAGE HEIGHT 0.4

(b) IMAGE HEIGHT 0.3

(c) IMAGE HEIGHT 0.2

(d) IMAGE HEIGHT 0.1

(e) IMAGE HEIGHT 0.0

(f) IMAGE HEIGHT −0.2

(g) IMAGE HEIGHT −0.4

—— C-LINE (656.2700 NM)
---- d-LINE (587.5600 NM)
—·— F-LINE (486.1300 NM)

FIG. 21
NEAR POINT
(a) IMAGE HEIGHT 0.4
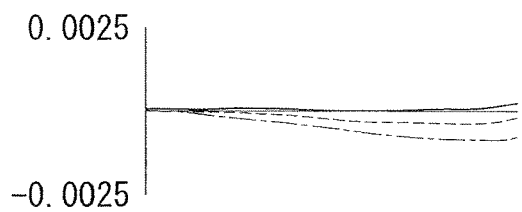
(b) IMAGE HEIGHT 0.3
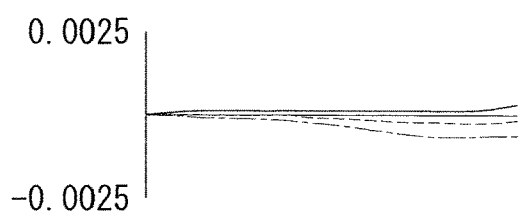
(c) IMAGE HEIGHT 0.2
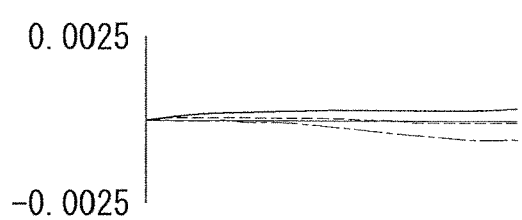
(d) IMAGE HEIGHT 0.1
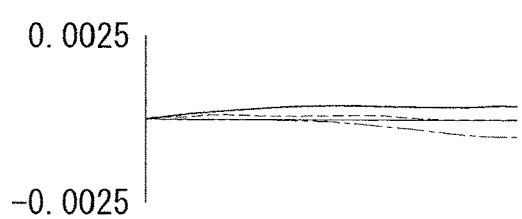
(e) IMAGE HEIGHT 0.0
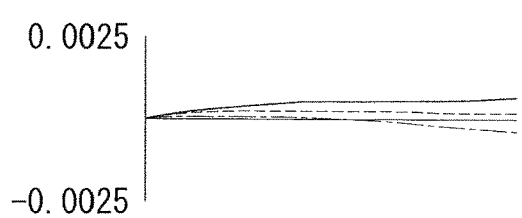
(f) IMAGE HEIGHT -0.2
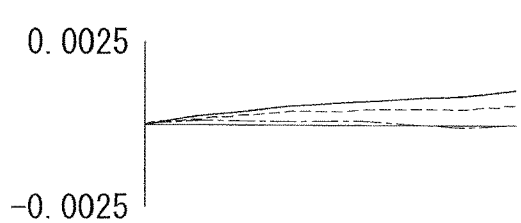
(g) IMAGE HEIGHT -0.4
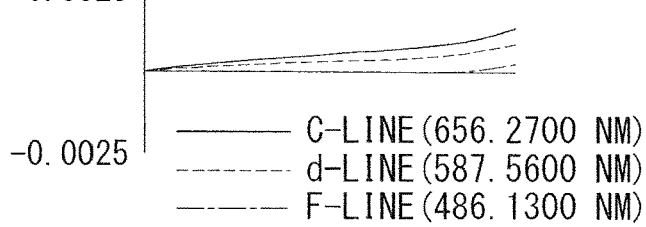
——— C-LINE (656.2700 NM)
- - - - d-LINE (587.5600 NM)
—·—·— F-LINE (486.1300 NM)

FIG. 24
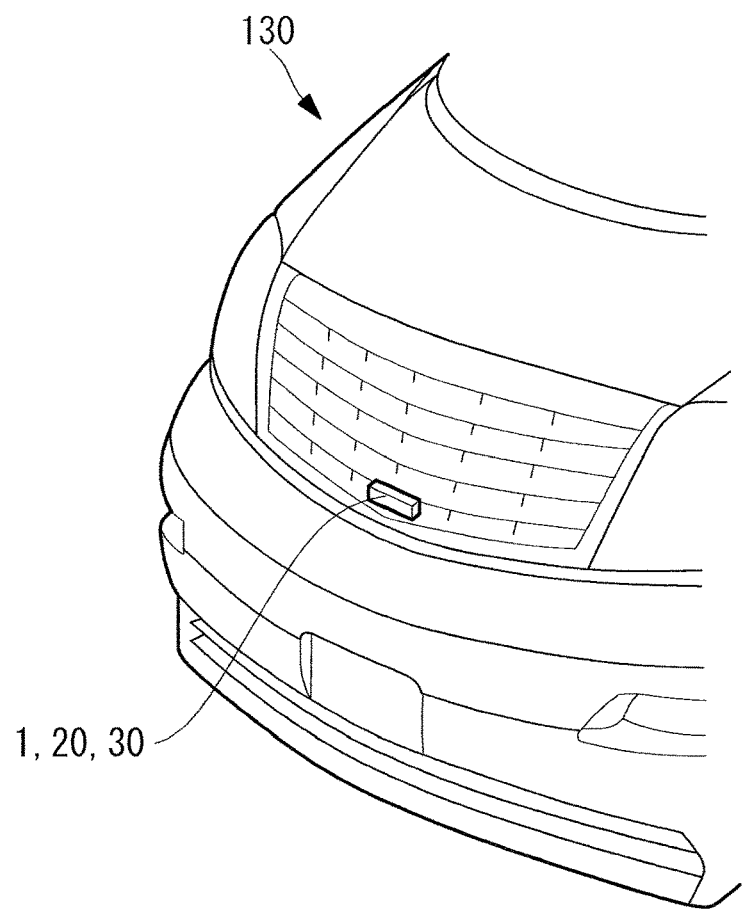
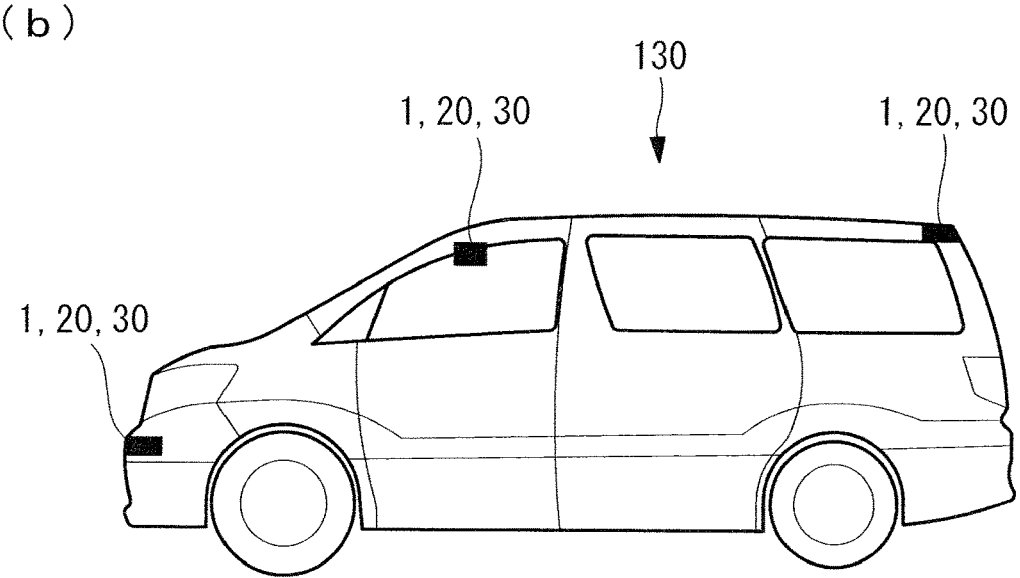

IMAGE-ACQUISITION APPARATUS

CROSS-REFERENCE TO RELATED APPLICATIONS

This is a continuation of International Application PCT/JP2015/071707 which is hereby incorporated by reference herein in its entirety.

TECHNICAL FIELD

The present invention relates to an image-acquisition apparatus.

BACKGROUND ART

There is a known stereoscopic endoscope apparatus that captures a three-dimensional image in which the zooming magnification can be changed and that captures a two-dimensional image of a large viewing field area (for example, see Patent Literature 1).

This stereoscopic endoscope apparatus is provided with, as an image-acquisition optical system: a zooming portion formed of a first lens group, a second lens group, and a third lens group that are configured based on a four-group zoom-type mechanical-correction zoom lens; and a pair of, that is, left and right, fourth lens groups of an imaging system disposed in a subsequent stage thereof.

During standard zooming, a moving mechanism that moves the second lens group and the third lens group of the zooming portion is controlled to change the zooming magnification, and, during image shifting, a moving mechanism that moves the third lens group and the fourth lens groups is controlled to enlarge the entire viewing field area in the left and right directions.

CITATION LIST

Patent Literature

{PTL 1} Japanese Unexamined Patent Application, Publication No. 2014-140593

SUMMARY OF INVENTION

An aspect of the present invention is an image-acquisition apparatus including: an imaging optical system that forms two images having a parallax therebetween; and an image-acquisition device that is disposed closer to an image side than the imaging optical system is and that acquires the parallax images, wherein the imaging optical system is provided with, sequentially from an object side to the image side, a first negative lens group having a negative refractive power, a first positive lens group having a positive refractive power, and a second positive lens group having a positive refractive power, wherein the first positive lens group and the first negative lens group are disposed along a common center axis, wherein the second positive lens group is provided with two positive lens groups that are disposed next to each other in a parallax direction on either side of the common center axis so as to correspond to the respective parallax images and that individually have center axes, wherein two aperture stops having openings that are provided closer to the image side than the first positive lens group is and that are disposed next to each other in the parallax direction on either side of the common center axis so as to correspond to the respective parallax images are provided, and wherein, in the case in which only lenses in which two surfaces thereof, that is, an object-side surface and an image-side surface thereof, on the center axes are in contact with air serve as lens components, the first negative lens group is provided with a lens component having a negative refractive power on the extreme object side, the first positive lens group includes only one moving lens group that is moved along the common center axis when focusing, all of remaining lens components in the imaging optical system, excluding the moving lens group, remain still, and the moving lens group satisfies condition (1):

$$fm > (Dk \times \Delta D)/(ih \times 0.4), \quad (1)$$

where fm is an absolute value of a focal distance of the moving lens group, $\Delta D$ is a maximum movement amount of the moving lens group, ih is an image height of the parallax image, and Dk is a distance between center axes of the individual extreme-object-side lenses of the second positive lens group.

Another aspect of the present invention is an image-acquisition apparatus including: an imaging optical system that forms two images having a parallax therebetween; and an image-acquisition device that is disposed closer to an image side than the imaging optical system is and that acquires the parallax images, wherein the imaging optical system is provided with, sequentially from an object side to the image side, a first negative lens group having a negative refractive power, a first positive lens group having a positive refractive power, and a second positive lens group having a positive refractive power, wherein the first positive lens group and the first negative lens group are disposed along a common center axis, wherein the second positive lens group is provided with two positive lens groups that are disposed next to each other in a parallax direction on either side of the common center axis so as to correspond to the respective parallax images and that individually have center axes, wherein two aperture stops having openings that are provided closer to the image side than the first positive lens group is and that are disposed next to each other in the parallax direction on either side of the common center axis so as to correspond to the respective parallax images are provided, and wherein, in the case in which only lenses in which two surfaces thereof, that is, an object-side surface and an image-side surface thereof, on the center axes are in contact with air serve as lens components, the first negative lens group is provided with a lens component having a negative refractive power on the extreme object side, the first positive lens group includes only one moving lens group that is moved along the common center axis when focusing, all of remaining lens components in the imaging optical system, excluding the moving lens group, remain still, and a center of the opening of at least one of the aperture stops may be eccentrically disposed with respect to the center axis of the positive lens group that corresponds to the opening of the second positive lens group.

Another aspect of the present invention is an image-acquisition apparatus including: an imaging optical system that forms two images having a parallax therebetween; and an image-acquisition device that is disposed closer to an image side than the imaging optical system is and that acquires the parallax images, wherein the imaging optical system is provided with, sequentially from an object side to the image side, a first negative lens group having a negative refractive power, a first positive lens group having a positive refractive power, and a second positive lens group having a positive refractive power, wherein the first positive lens group and the first negative lens group are disposed along a common center axis, wherein the second positive lens group is provided with two positive lens groups that are disposed next to each other in a parallax direction on either side of the common center axis so as to correspond to the respective parallax images and that individually have center axes, wherein two aperture stops having openings that are provided closer to the image side than the first positive lens group is and that are disposed next to each other in the parallax direction on either side of the common center axis so as to correspond to the respective parallax images are provided, and wherein, in the case in which only lenses in which two surfaces thereof, that is, an object-side surface and an image-side surface thereof, on the center axes are in contact with air serve as lens components, the first negative lens group is provided with a lens component having a negative refractive power on the extreme object side, the first positive lens group includes only one moving lens group that is moved along the common center axis when focusing, all of remaining lens components in the imaging optical system, excluding the moving lens group, remain still, and the first negative lens group may be formed of two lens components including the lens component having the negative refractive power.

Another aspect of the present invention is an image-acquisition apparatus including: an imaging optical system that forms two images having a parallax therebetween; and an image-acquisition device that is disposed closer to an image side than the imaging optical system is and that acquires the parallax images, wherein the imaging optical system is provided with, sequentially from an object side to the image side, a first negative lens group having a negative refractive power, a first positive lens group having a positive refractive power, and a second positive lens group having a positive refractive power, wherein the first positive lens group and the first negative lens group are disposed along a common center axis, wherein the second positive lens group is provided with two positive lens groups that are disposed next to each other in a parallax direction on either side of the common center axis so as to correspond to the respective parallax images and that individually have center axes, wherein two aperture stops having openings that are provided closer to the image side than the first positive lens group is and that are disposed next to each other in the parallax direction on either side of the common center axis so as to correspond to the respective parallax images are provided, and wherein, in the case in which only lenses in which two surfaces thereof, that is, an object-side surface and an image-side surface thereof, on the center axes are in contact with air serve as lens components, the first negative lens group is provided with a lens component having a negative refractive power on the extreme object side, the first positive lens group includes only one moving lens group that is moved along the common center axis when focusing, all of remaining lens components in the imaging optical system, excluding the moving lens group, remain still, and the second positive lens group may satisfy the following condition (3):

$$0.1 < fa/f2p < 0.4, \quad (3)$$

where fa is a focal distance when focusing on a far object by arranging, on a straight line, the individual center axes of the first negative lens group, the first positive lens group, and the second positive lens group by moving the second positive lens group in a direction substantially orthogonal to the common center axis of the first negative lens group and the first positive lens group, and f2p is a focal distance of the second positive lens group.

Another aspect of the present invention is an image-acquisition apparatus including: an imaging optical system that forms two images having a parallax therebetween; and an image-acquisition device that is disposed closer to an image side than the imaging optical system is and that acquires the parallax images, wherein the imaging optical system is provided with, sequentially from an object side to the image side, a first negative lens group having a negative refractive power, a first positive lens group having a positive refractive power, and a second positive lens group having a positive refractive power, wherein the first positive lens group and the first negative lens group are disposed along a common center axis, wherein the second positive lens group is provided with two positive lens groups that are disposed next to each other in a parallax direction on either side of the common center axis so as to correspond to the respective parallax images and that individually have center axes, wherein two aperture stops having openings that are provided closer to the image side than the first positive lens group is and that are disposed next to each other in the parallax direction on either side of the common center axis so as to correspond to the respective parallax images are provided, and wherein, in the case in which only lenses in which two surfaces thereof, that is, an object-side surface and an image-side surface thereof, on the center axes are in contact with air serve as lens components, the first negative lens group is provided with a lens component having a negative refractive power on the extreme object side, the first positive lens group includes only one moving lens group that is moved along the common center axis when focusing, all of remaining lens components in the imaging optical system, excluding the moving lens group, remain still, the first positive lens group may be formed of two positive lens component and one negative lens component, and the moving lens group may be any one of the positive lens components of the first positive lens group.

In the above-described aspect, it is preferable that condition (5) be satisfied:

$$\text{a maximum angle of view is equal to or greater than } 100° \text{ when focusing on a far object.} \quad (5)$$

In the above-described aspect, it is preferable that condition (6) be satisfied:

$$0.2 < D01 < 2, \quad (6)$$

where D01 is a distance between entrance pupil surfaces.

Figure 2:
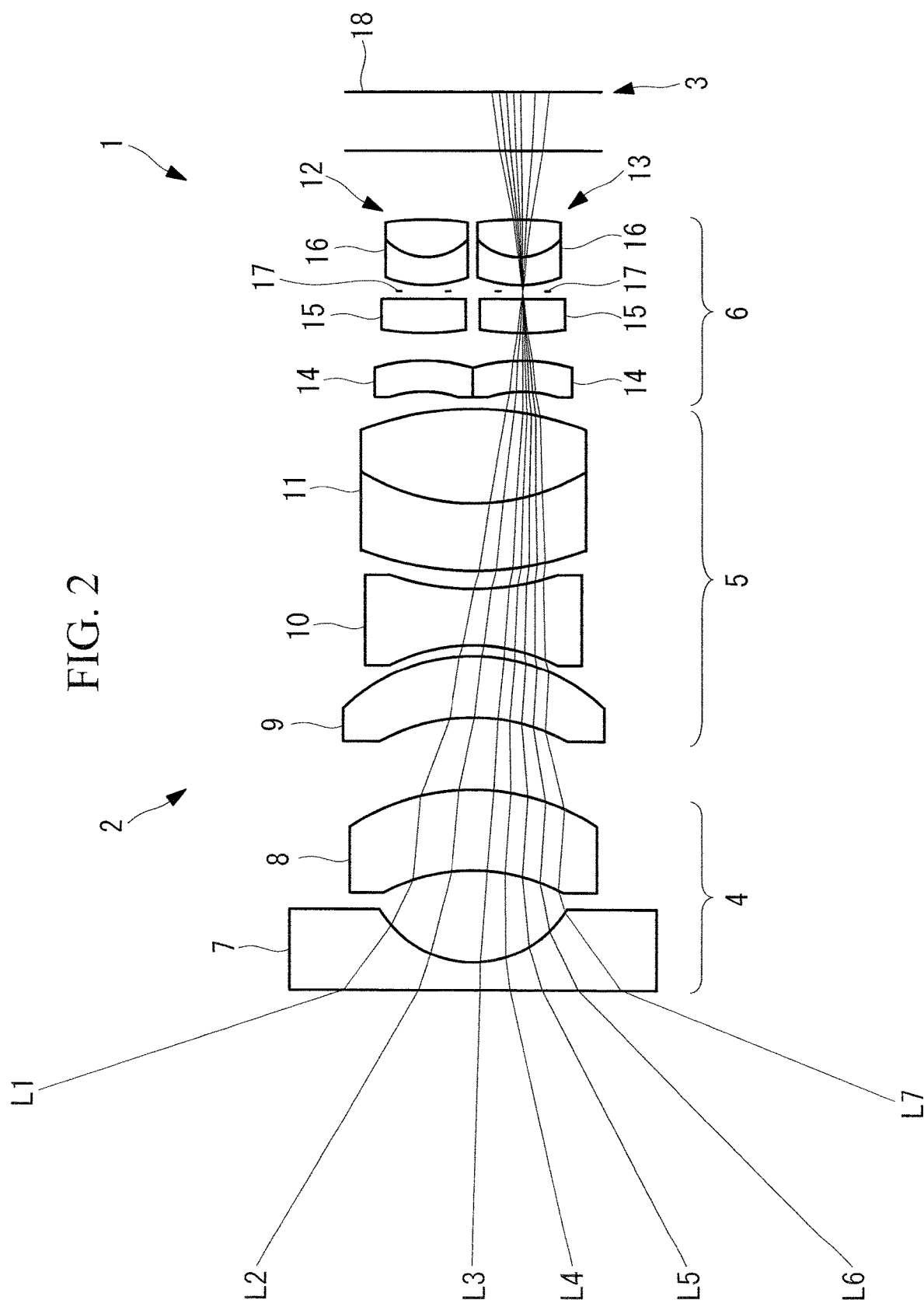
FIG. 2 is a diagram showing ray tracing of principle rays when the moving lens group of the image-acquisition apparatus in FIG. 1 is placed at a near-point position (position of the moving lens group when focusing on an object at a nearest point).
Figure 3:
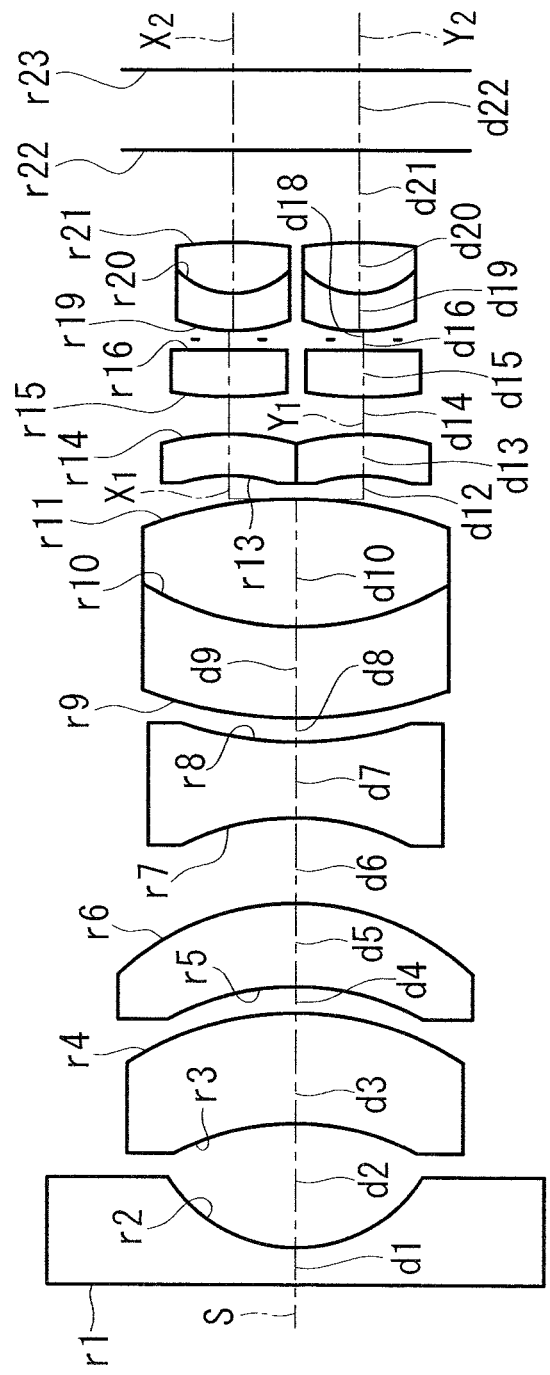
FIG. 3 is a diagram showing a lens arrangement of an imaging optical system according to an example of the image-acquisition apparatus in FIG. 1.
Figure 4:
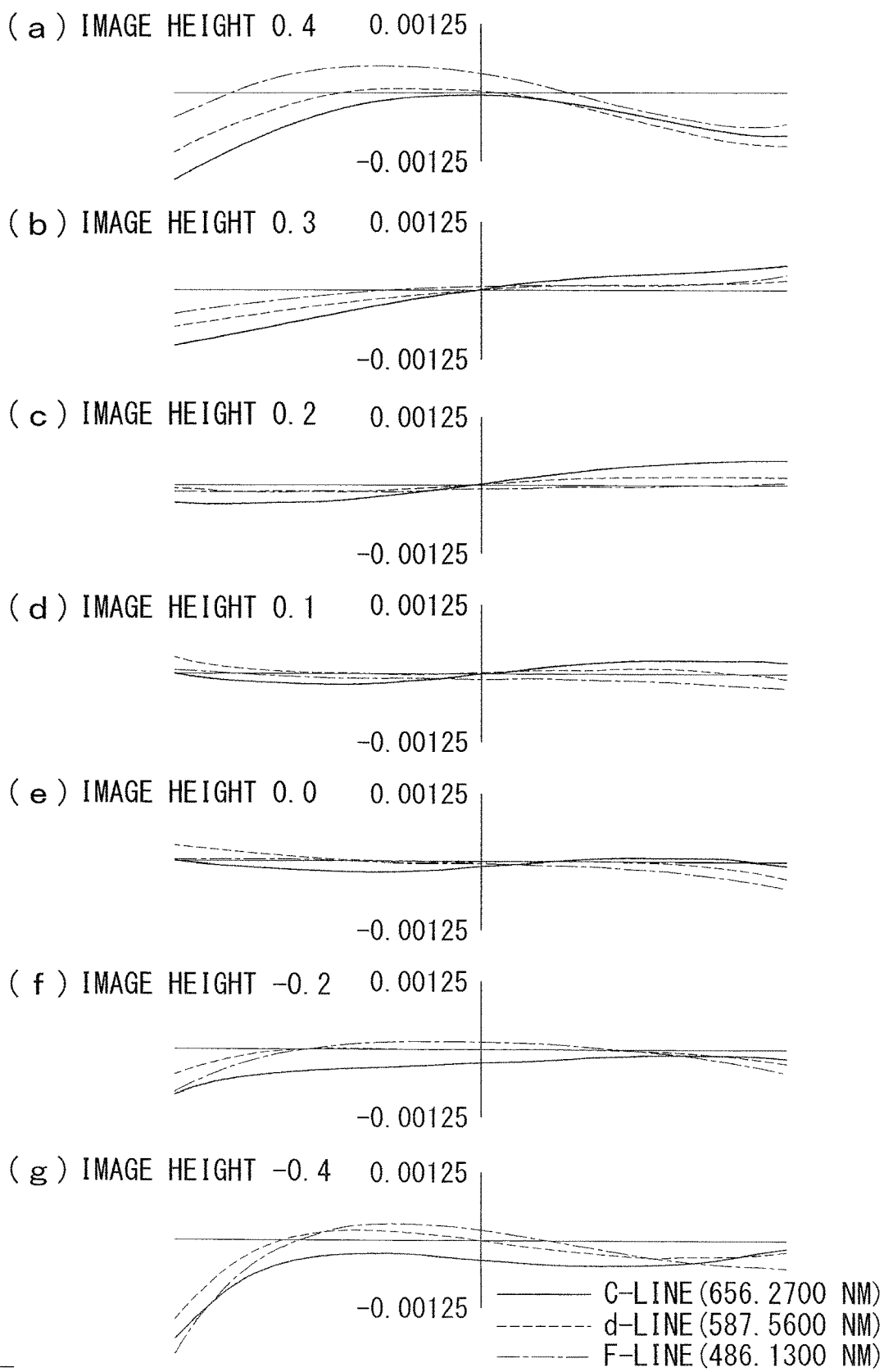
FIG. 4 is a diagram showing lateral aberrations in a direction along the plane of the figure (Y-direction) for a light bundle that includes (a) a light beam L7, (b) a light beam L6, (c) a light beam L5, (d) a light beam L4, (e) a light beam L3, (f) a light beam L2, and (g) a light beam L1 serving as principal rays in the case in which the moving lens group of the imaging optical system in FIG. 3 is placed at the far-point position shown in FIG. 2.

FIG. 5 is a diagram showing lateral aberrations in a direction perpendicular to the plane of the figure (X-direction) for a light bundle that includes (a) the light beam L7, (b) the light beam L6, (c) the light beam L5, (d) the light beam L4, (e) the light beam L3, (f) the light beam L2, and (g) the light beam L1 serving as principal rays in the case in which the moving lens group of the imaging optical system in FIG. 3 is placed at the far-point position shown in FIG. 2.

Figure 1:
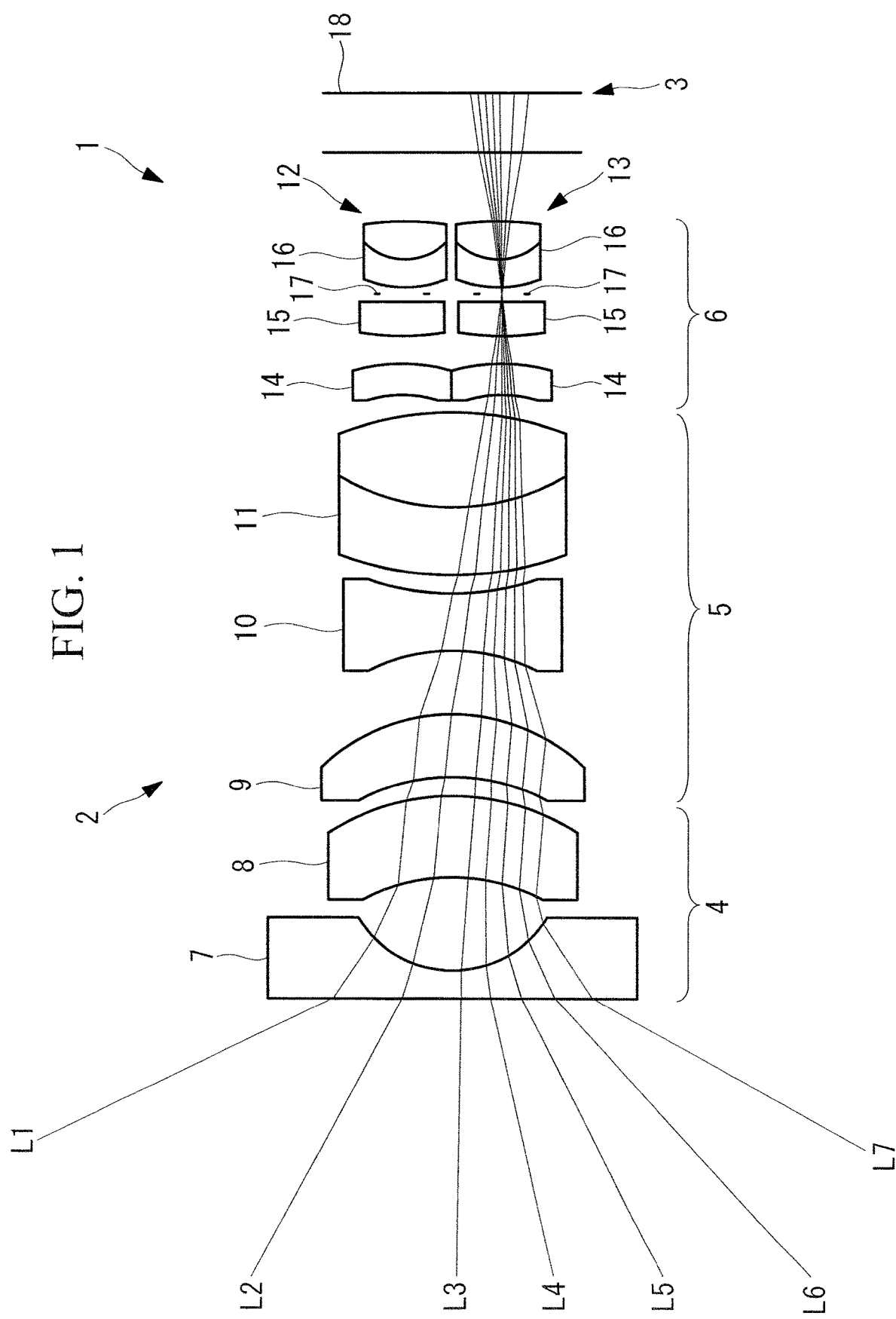
FIG. 1 is a diagram showing ray tracing of principal rays when a moving lens group of an image-acquisition apparatus according to a first embodiment of the present invention is placed at a far-point position (position of the moving lens group when focusing on an object at a farthest point).

FIG. 6 is a diagram showing lateral aberrations in the Y-direction for the light bundle that includes (a) the light beam L7, (b) the light beam L6, (c) the light beam L5, (d) the light beam L4, (e) the light beam L3, (f) the light beam L2, and (g) the light beam L1 serving as the principal rays in the case in which the moving lens group of the imaging optical system in FIG. 3 is placed at the near-point position shown in FIG. 1.

FIG. 7 is a diagram showing lateral aberrations in the X-direction for the light bundle that includes (a) the light beam L7, (b) the light beam L6, (c) the light beam L5, (d) the light beam L4, (e) the light beam L3, (f) the light beam L2, and (g) the light beam L1 serving as the principal rays in the case in which the moving lens group of the imaging optical system in FIG. 3 is placed at the near-point position shown in FIG. 1.

Figure 8:
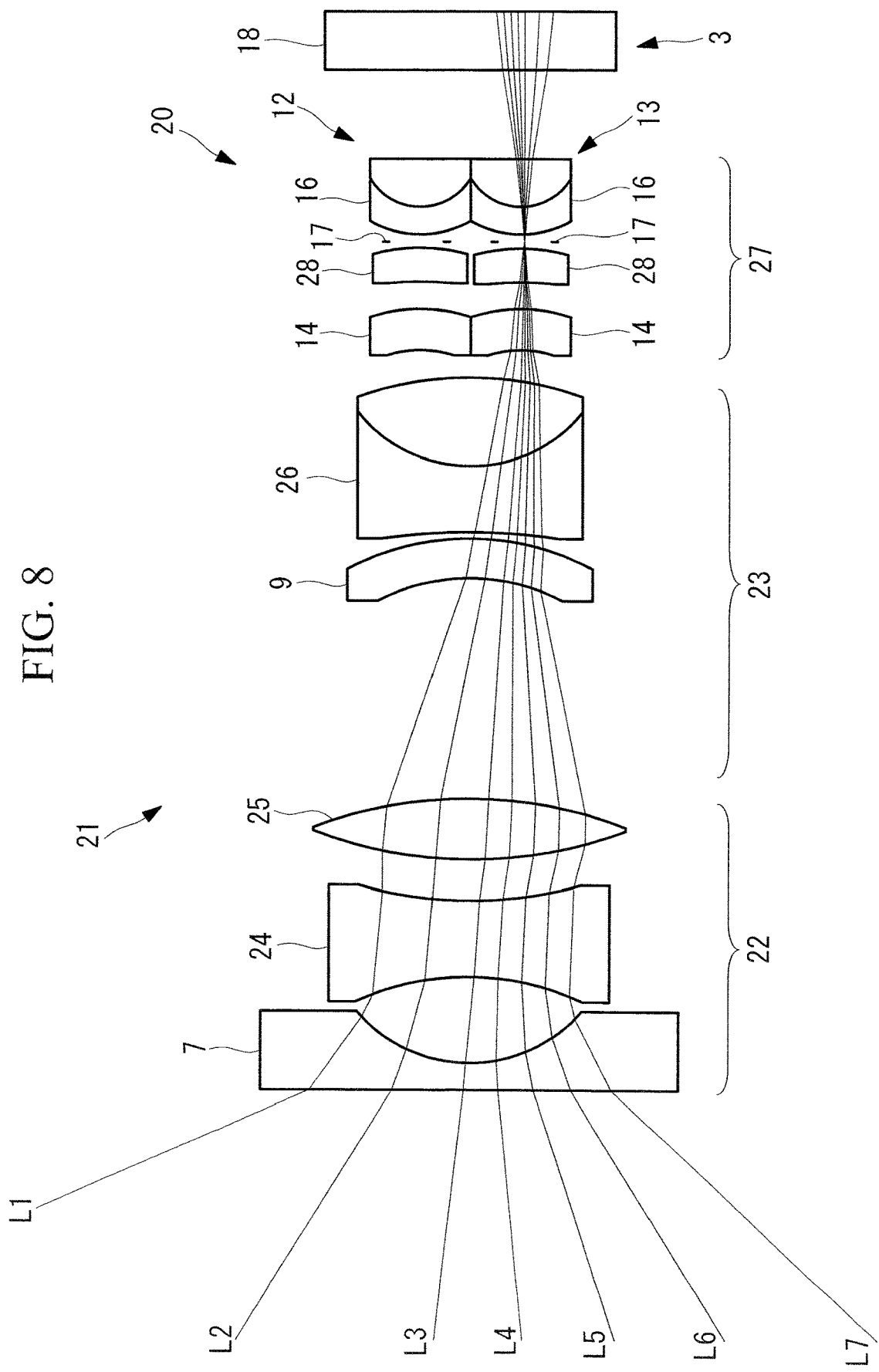

FIG. 8 is a diagram showing ray tracing of principal rays when a moving lens group of an image-acquisition apparatus according to a second embodiment of the present invention is placed at a far-point position.

Figure 9:
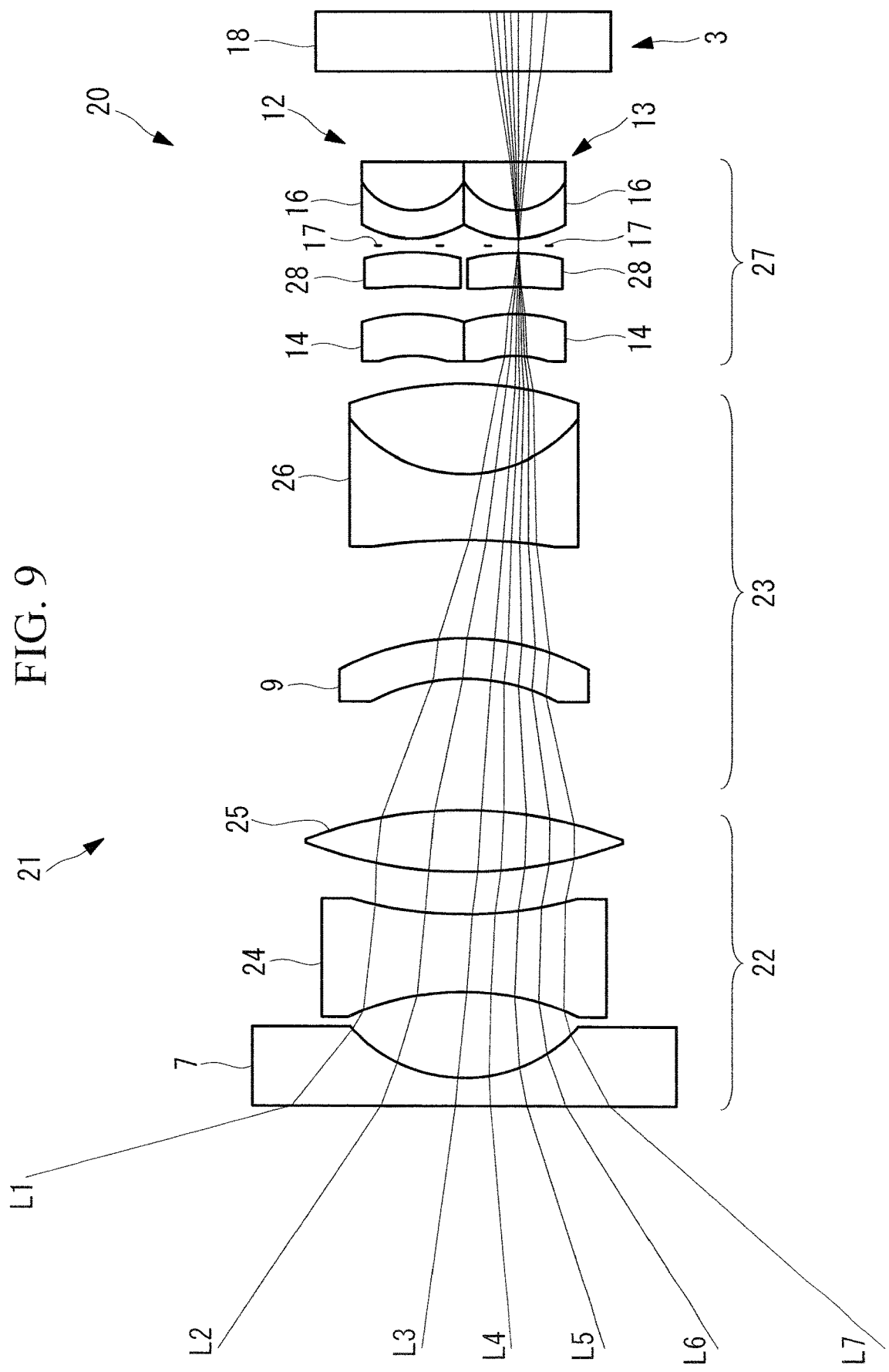

FIG. 9 is a diagram showing ray tracing of principle rays when the moving lens group of the image-acquisition apparatus in FIG. 8 is placed at a near-point position.

Figure 10:
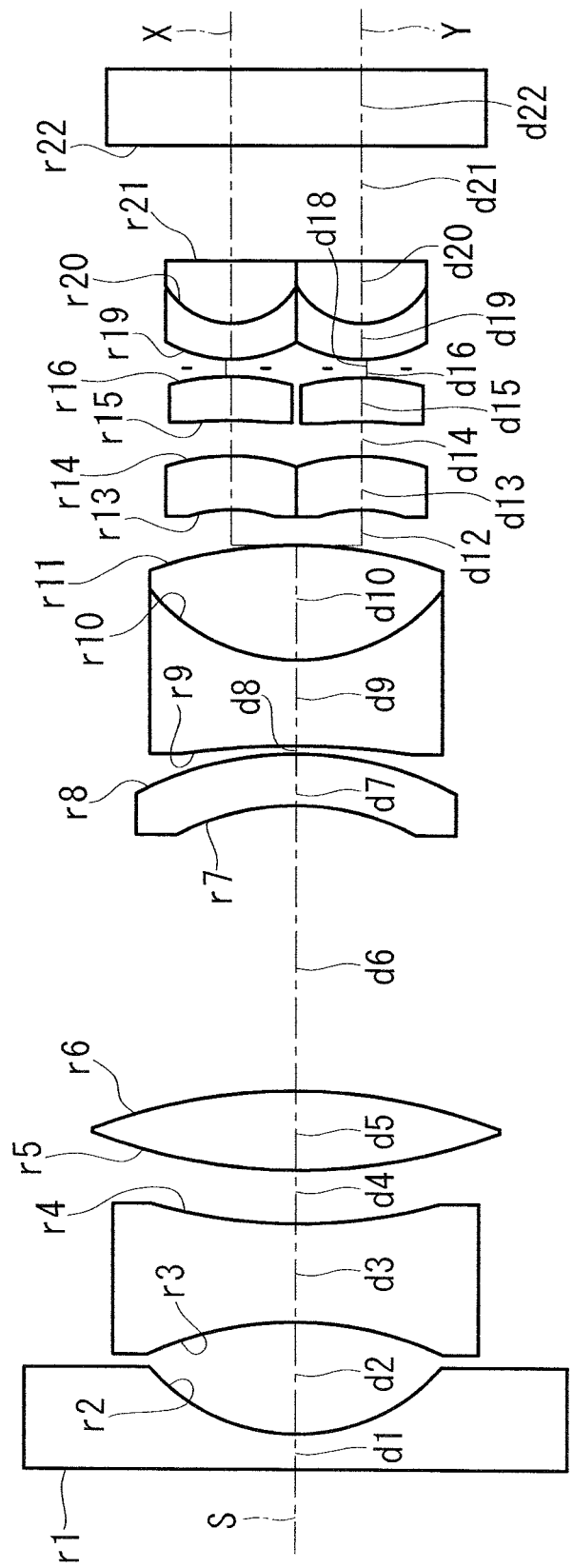

FIG. 10 is a diagram showing a lens arrangement of an imaging optical system according to an example of the image-acquisition apparatus in FIG. 8.

Figure 11:
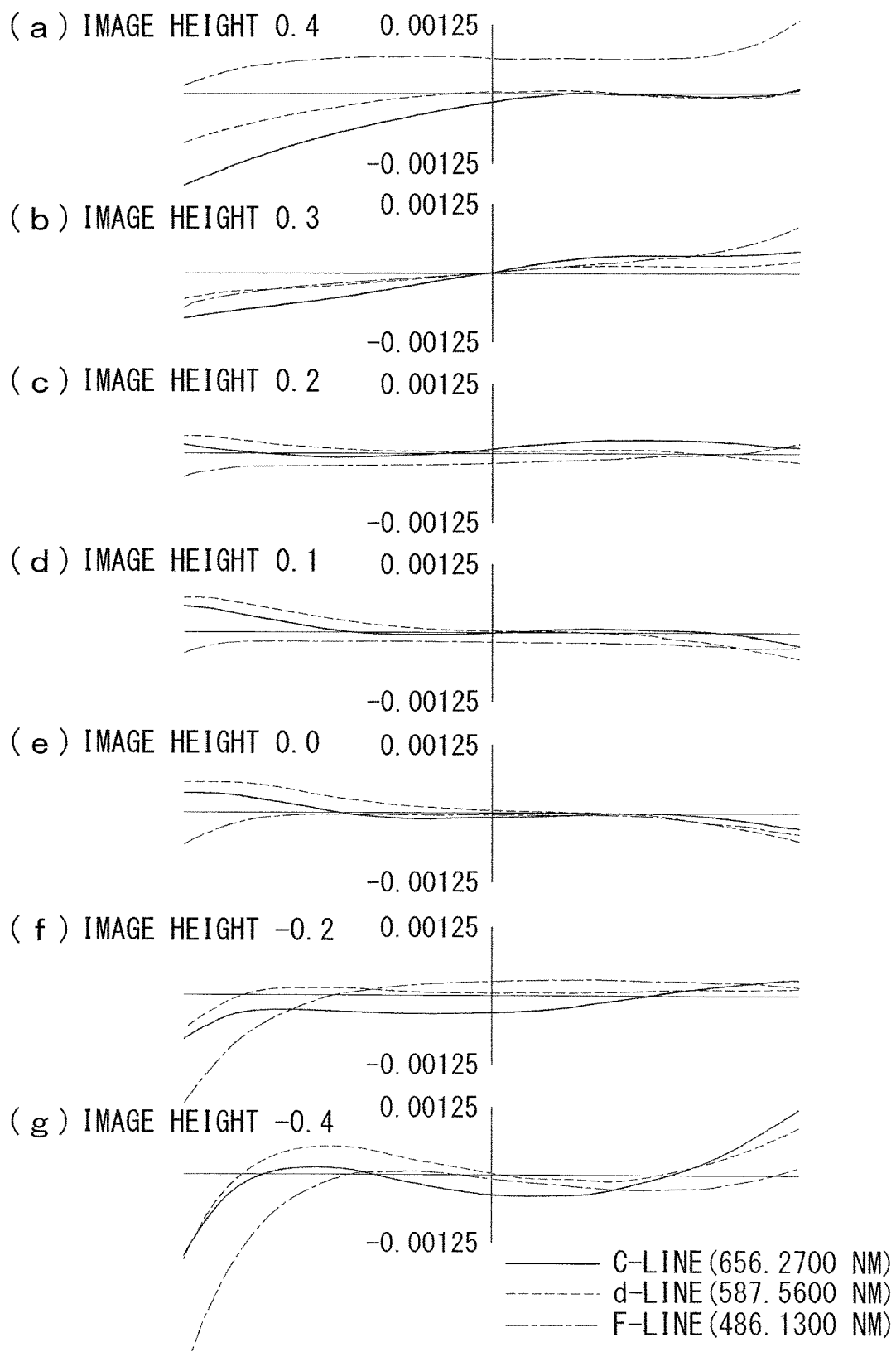

FIG. 11 is a diagram showing comatic aberrations of (a) a light beam L1, (b) a light beam L2, (c) a light beam L3, (d) a light beam L4, (e) a light beam L5, (f) a light beam L6, and (g) a light beam L7 in the case in which the moving lens group of the imaging optical system in FIG. 10 is placed at the far-point position in FIG. 8.

FIG. 12 is a diagram showing magnification chromatic aberrations of (a) the light beam L1, (b) the light beam L2, (c) the light beam L3, (d) the light beam L4, (e) the light beam L5, (f) the light beam L6, and (g) the light beam L7 in the case in which the moving lens group of the imaging optical system in FIG. 10 is placed at the far-point position shown in FIG. 8.

Figure 13:
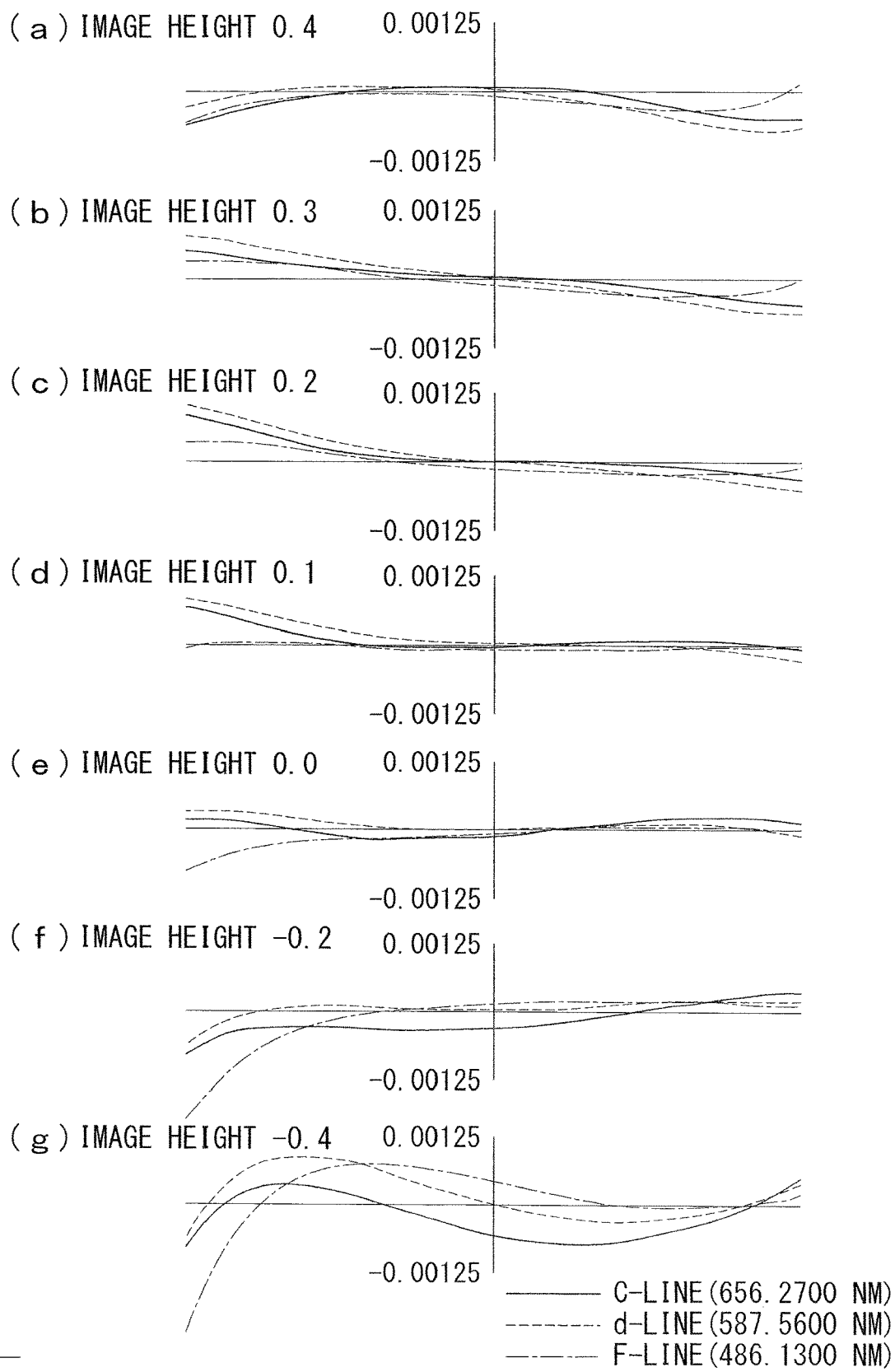

FIG. 13 is a diagram showing comatic aberrations of (a) the light beam L1, (b) the light beam L2, (c) the light beam L3, (d) the light beam L4, (e) the light beam L5, (f) the light beam L6, and (g) the light beam L7 in the case in which the moving lens group of the imaging optical system in FIG. 10 is placed at the near-point position shown in FIG. 9.

Figure 14:
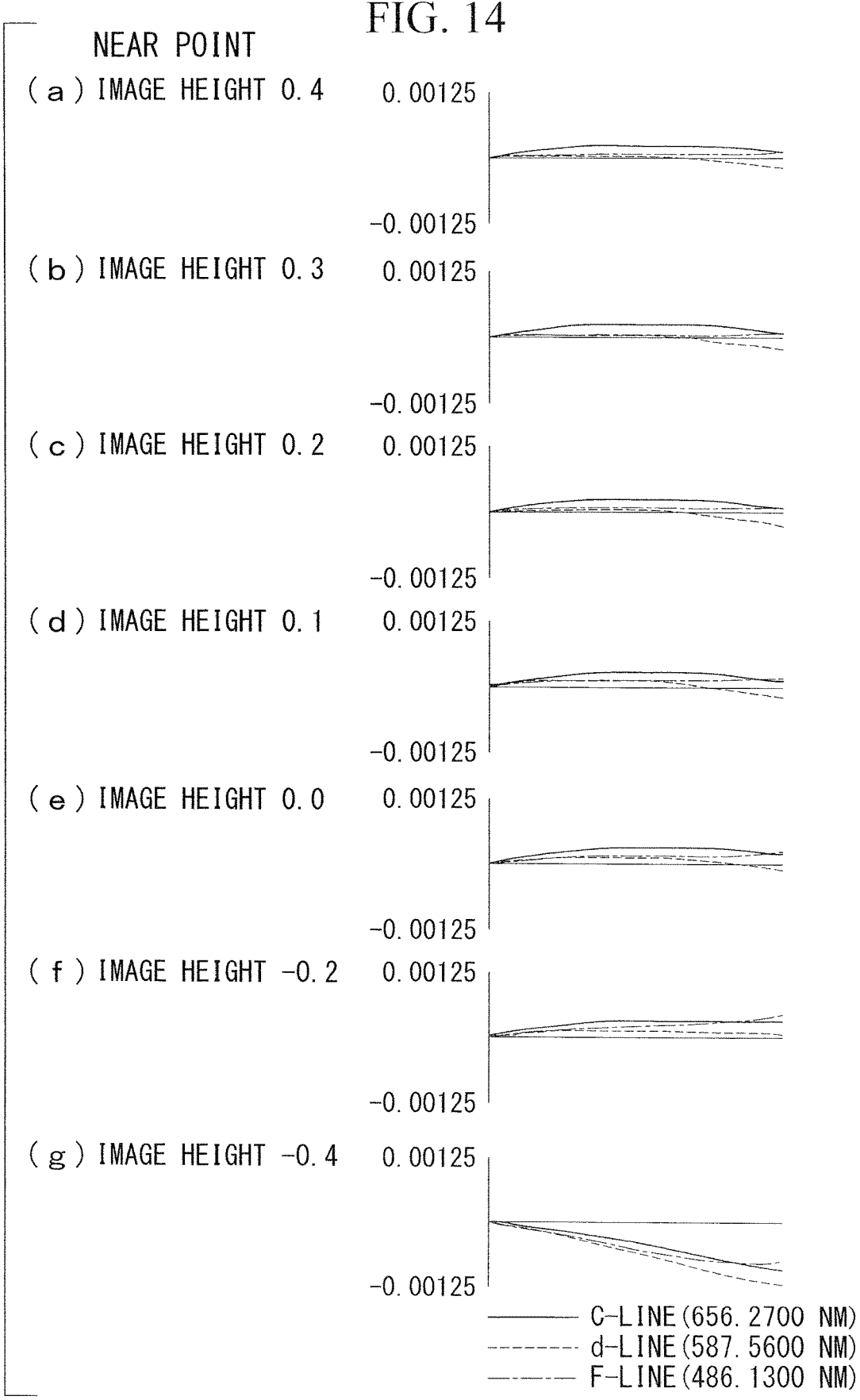

FIG. 14 is a diagram showing magnification chromatic aberrations of (a) the light beam L1, (b) the light beam L2, (c) the light beam L3, (d) the light beam L4, (e) the light beam L5, (f) the light beam L6, and (g) the light beam L7 in the case in which the moving lens group of the imaging optical system in FIG. 10 is placed at the near-point position shown in FIG. 9.

Figure 15:
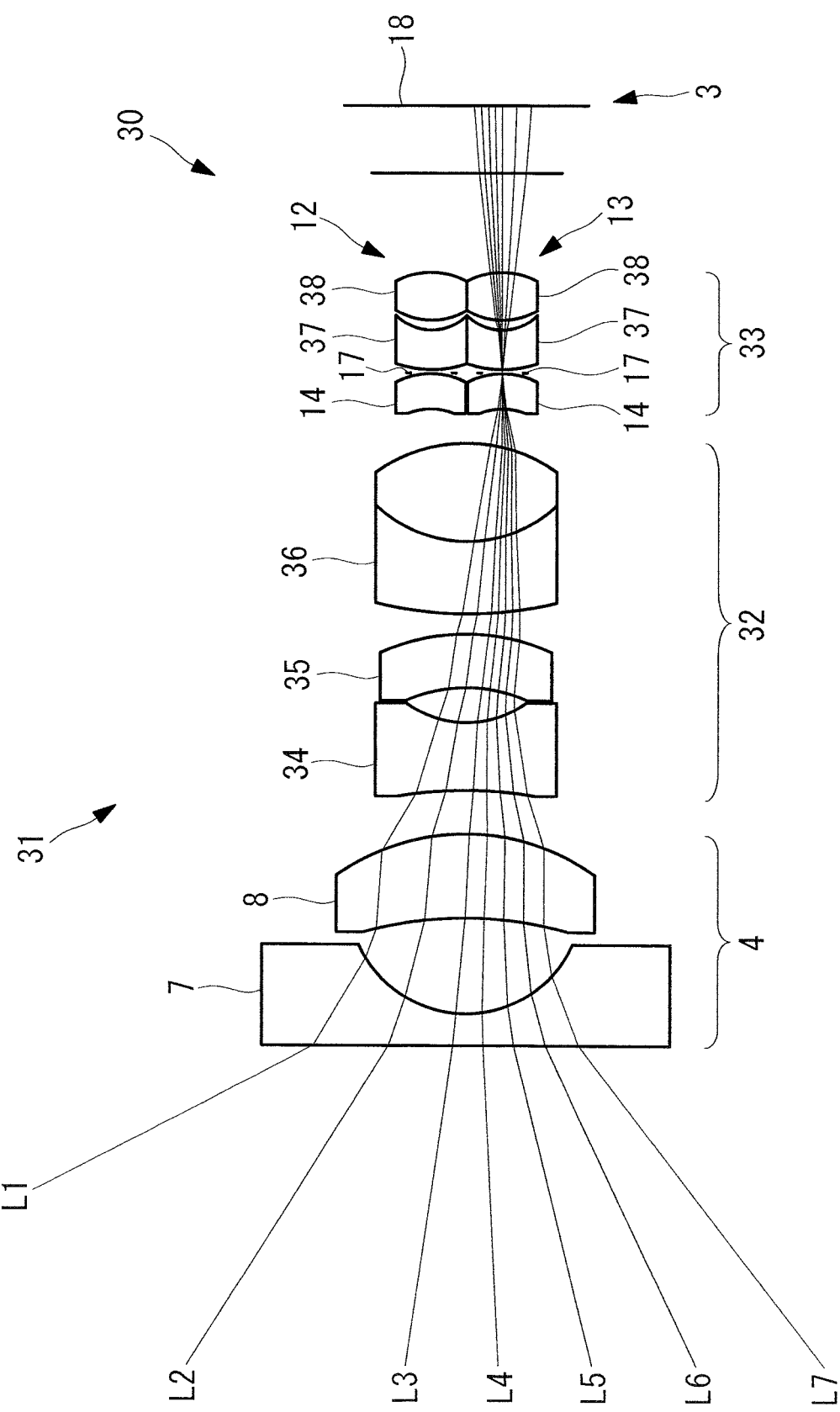

FIG. 15 is a diagram showing ray tracing of principal rays when a moving lens group of an image-acquisition apparatus according to a third embodiment of the present invention is placed at a far-point position.

Figure 16:
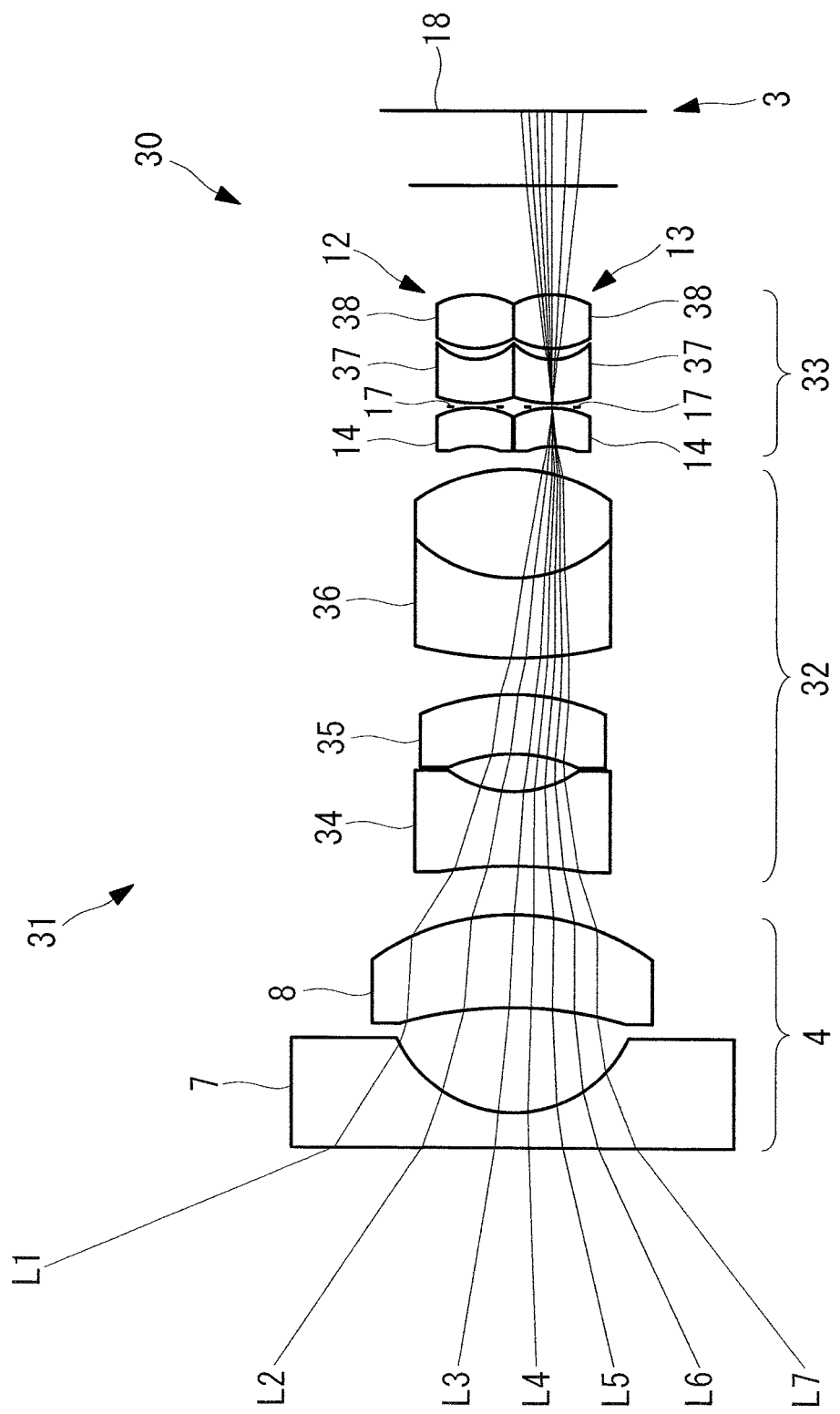

FIG. 16 is a diagram showing ray tracing of principle rays when the moving lens group of the image-acquisition apparatus in FIG. 15 is placed at a near-point position.

Figure 17:
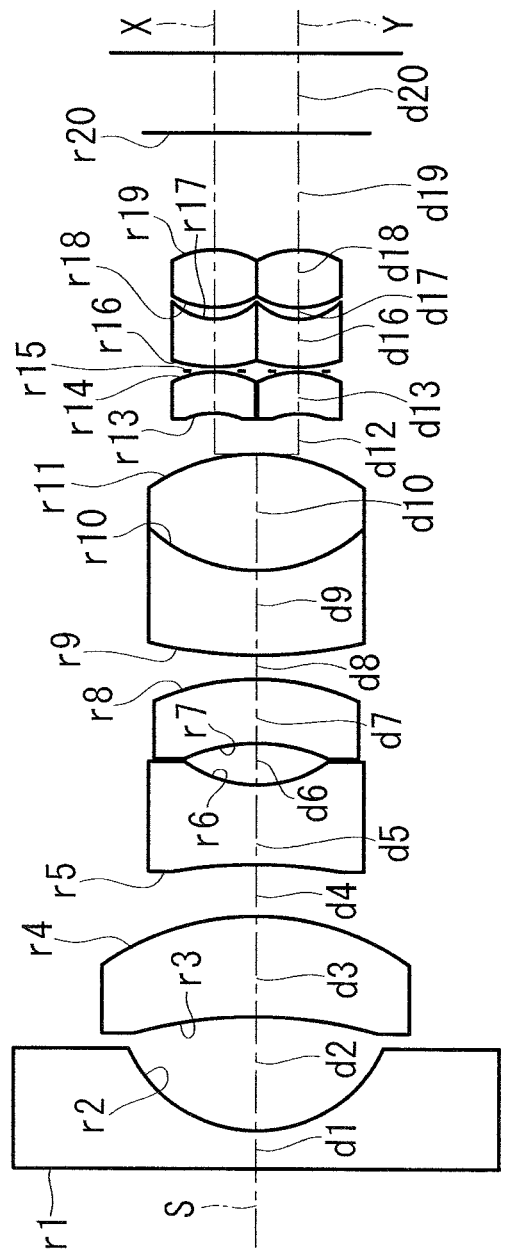

FIG. 17 is a diagram showing a lens arrangement of an imaging optical system according to an example of the image-acquisition apparatus in FIG. 15.

Figure 18:
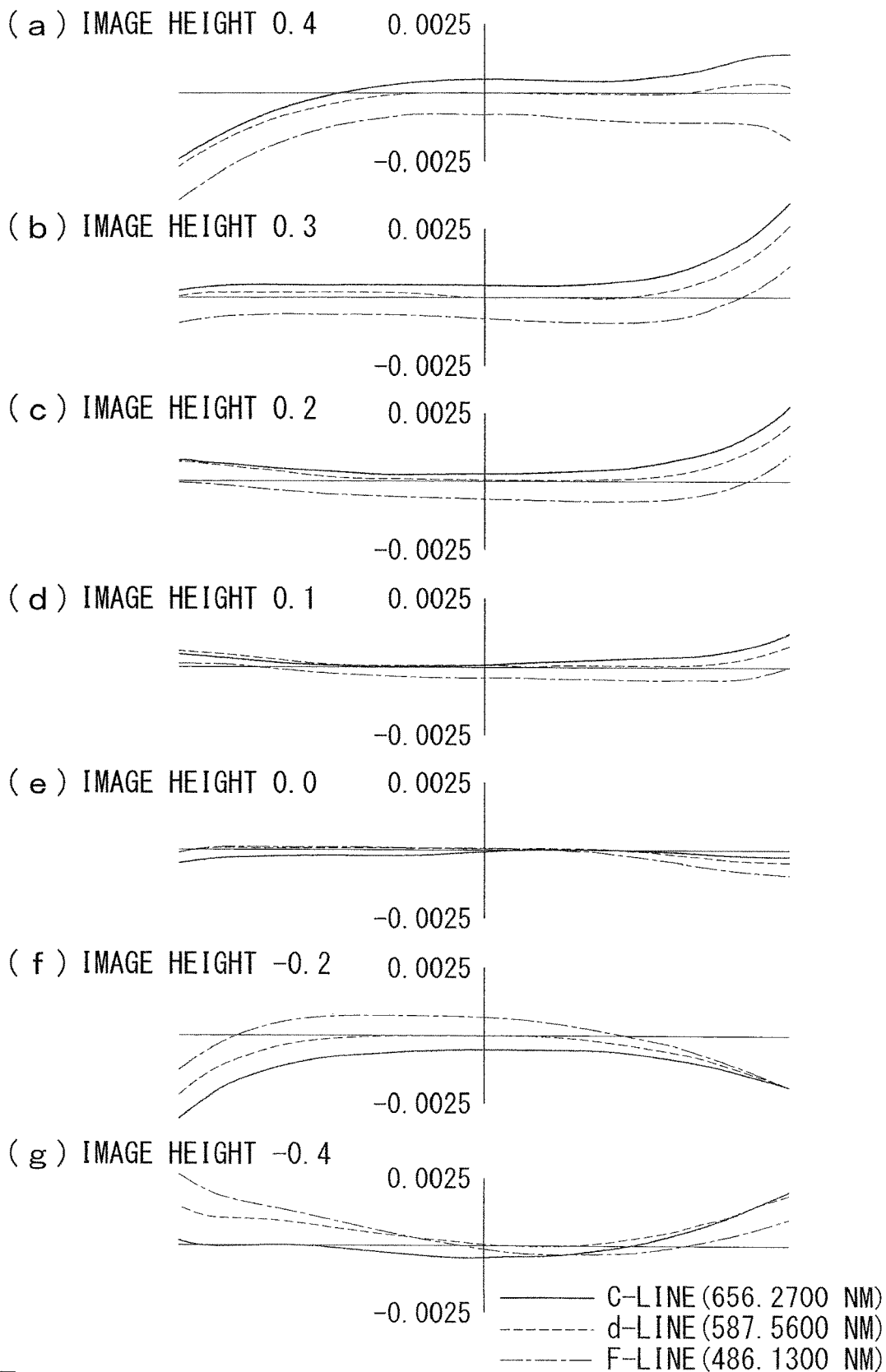

FIG. 18 is a diagram showing lateral aberrations in the Y-direction for the light bundle that includes (a) the light beam L1, (b) the light beam L2, (c) the light beam L3, (d) the light beam L4, (e) the light beam L5, (f) the light beam L6, and (g) the light beam L7 serving as the principal rays in the case in which the moving lens group of the imaging optical system in FIG. 17 is placed at the far-point position shown in FIG. 15.

FIG. 19 is a diagram showing lateral aberrations in the X-direction for the light bundle that includes (a) the light beam L7, (b) the light beam L6, (c) the light beam L5, (d) the light beam L4, (e) the light beam L3, (f) the light beam L2, and (g) the light beam L1 serving as the principal rays in the case in which the moving lens group of the imaging optical system in FIG. 17 is placed at the far-point position shown in FIG. 15.

FIG. 20 is a diagram showing lateral aberrations in the Y-direction for the light bundle that includes (a) the light beam L7, (b) the light beam L6, (c) the light beam L5, (d) the light beam L4, (e) the light beam L3, (f) the light beam L2, and (g) the light beam L1 serving as the principal rays in the case in which the moving lens group of the imaging optical system in FIG. 17 is placed at the near-point position shown in FIG. 16.

FIG. 21 is a diagram showing lateral aberrations in the X-direction for the light bundle that includes (a) the light beam L7, (b) the light beam L6, (c) the light beam L5, (d) the light beam L4, (e) the light beam L3, (f) the light beam L2, and (g) the light beam L1 serving as the principal rays in the case in which the moving lens group of the imaging optical system in FIG. 17 is placed at the near-point position shown in FIG. 16.

Figure 22:
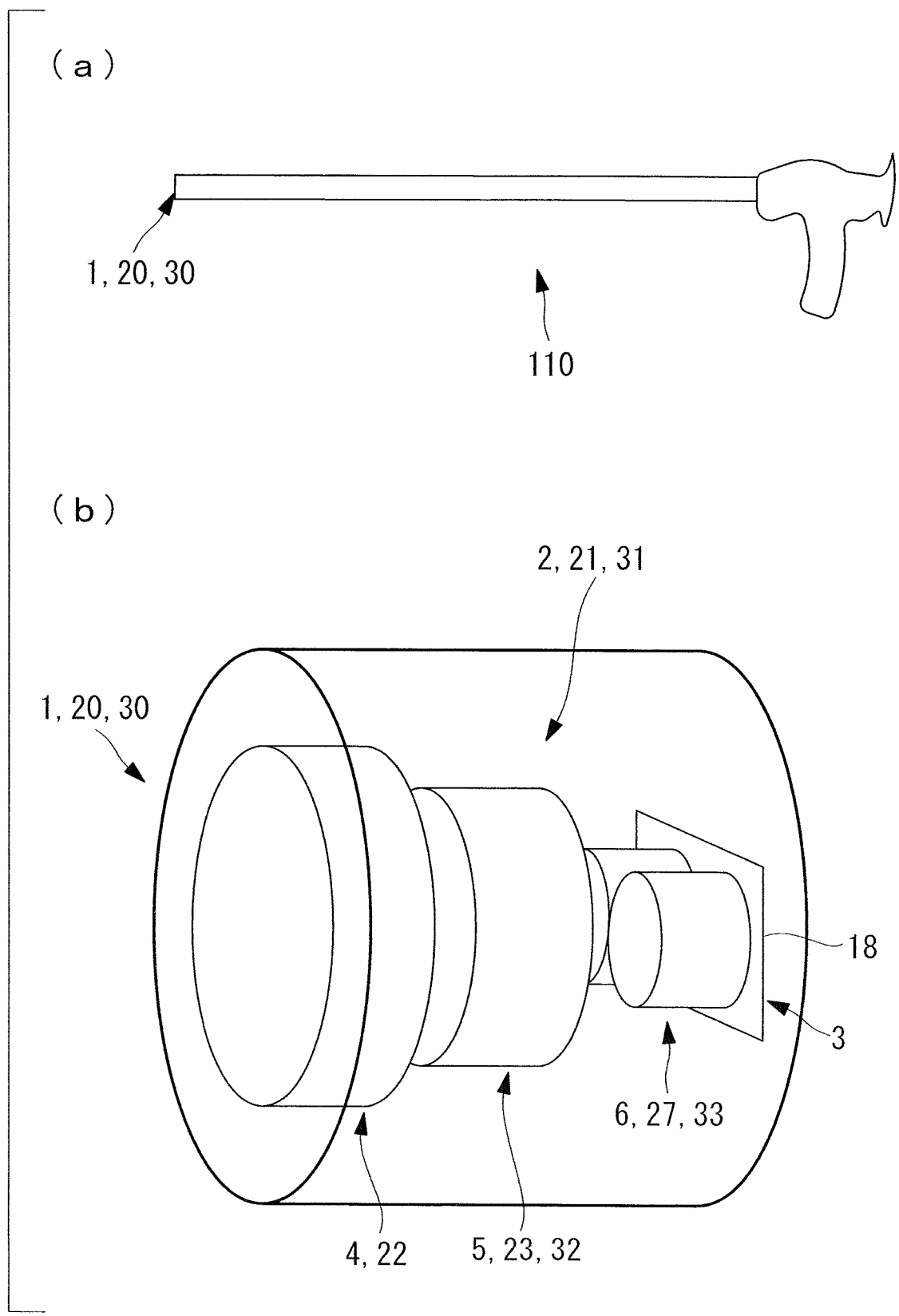

FIG. 22 shows (a) an overall view of and (b) a perspective view of a distal-end portion of a rigid endoscope to which the image-acquisition apparatuses according to the respective embodiments are applied.

Figure 23:
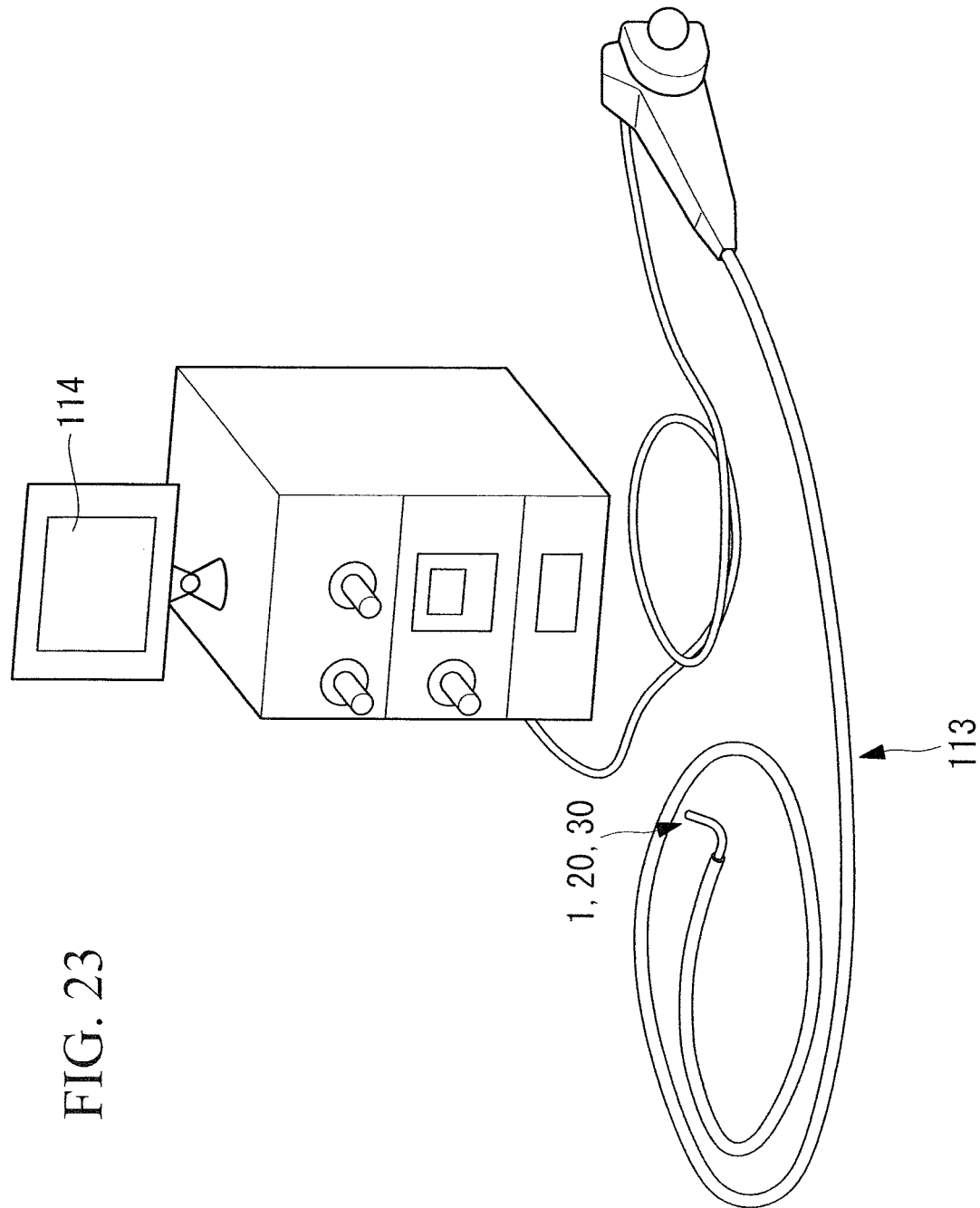

FIG. 23 is an overall diagram of a flexible endoscope to which the image-acquisition apparatuses according to the respective embodiments are applied.

FIG. 24 is (a) a perspective view of a front portion of and (b) a side view of an automobile to which the image-acquisition apparatuses according to the respective embodiments are applied.

DESCRIPTION OF EMBODIMENTS

An image-acquisition apparatus 1 according to a first embodiment of the present invention will be described below with reference to the drawings.

As shown in FIGS. 1 and 2, the image-acquisition apparatus 1 according to this embodiment is provided with an imaging optical system 2 and an image-acquisition device 3.

The imaging optical system 2 is provided with, sequentially from an object side to an image side: a first negative lens group 4 having a negative refractive power; a first positive lens group 5 having a positive refractive power; and a second positive lens group 6 having a positive refractive power.

The first negative lens group 4 is provided with, sequentially from the object side: a plano-concave lens (negative-refractive-power lens component) 7 having a concave surface on the image side; and a single meniscus lens 8 having a concave surface on the object side.

The first positive lens group 5 is provided with, sequentially from the object side: a single meniscus lens (moving lens group) 9 having a concave surface on the object side; and a biconcave lens 10; and a doublet 11 formed of a meniscus lens having a convex surface on the object side and a biconvex lens.

As shown in FIG. 3, the first negative lens group 4 and the first positive lens group 5 are disposed along a common center axis (common center axis) S, and the meniscus lens 9 of the first positive lens group 5 is provided so as to be movable along the center axis S.

As shown in FIG. 3, the second positive lens group 6 is provided with two positive lens groups 12 and 13 that are disposed on either side of the common center axis S so as to have spaces on both sides thereof and that individually have center axes (X1 or X2) and (Y1 or Y2). Each of the positive lens groups 12 and 13 is provided with: a negative meniscus lens 14 having a concave surface on the object side; a positive meniscus lens 15 having a convex surface on the object side; a doublet 16 that is formed of a meniscus lens having a convex surface on the object side and a biconvex lens; and an aperture stop 17 that has an opening and that is disposed between the positive meniscus lens 15 and the doublet 16.

When light coming from the object enters the second positive lens group 6 by passing through the first positive lens group 5 after being focused by the first negative lens group 4, the light is separated in accordance with parallax, and thus, two parallax images are formed by the individual positive lens groups 12 and 13 constituting the second positive lens group 6.

The image-acquisition device 3 is constituted of a CCD, a CMOS device, or the like in which an image-acquisition surface 18 is disposed at the position at which the parallax image is formed by the second positive lens group 6. A parallel flat plate that represents a cover glass or an infrared cut filter in the image-acquisition device 3 and that is optically equivalent thereto is disposed immediately before the image-acquisition surface 18.

The image-acquisition apparatus 1 according to this embodiment satisfies the following conditions (1) to (6):

$$fm > (Dk \times \Delta D)/(ih \times 0.4); \quad (1)$$

$$fm/f1n1p < 10; \quad (2)$$

$$0.1 < fa/f2p < 0.4; \quad (3)$$

$$2 < |ra/Dk| < 20; \quad (4)$$

The maximum angle of view is equal to or greater than 100° when focusing on a far object; (5)

$$0.2 < D01 < 2; \text{ and} \quad (6)$$

Here,
fm is the absolute value of the focal distance of the meniscus lens 9;
$\Delta D$ is the maximum movement amount of the meniscus lens 9;
ih is the image height of the parallax image;
Dk is the distance between the center axes X1 and Y1 of the individual negative meniscus lenses (extreme-object-side lenses) 14 of the two positive lens groups 12 and 13 constituting the second positive lens group 6;
f1n1p is the absolute value of the combined focal distance of the first negative lens group 4 and the first positive lens group 5 during far focusing;
fa is the focal distance when focusing on a far object by arranging, on a straight line, the individual center axes S, X1, and X2 of the first negative lens group 4, the first positive lens group 5 and the second positive lens group 6 by moving the second positive lens group 6 in a direction orthogonal to the common center axis S of the first negative lens group 4 and the first positive lens group 5;
f2p is the focal distance of the second positive lens group 6;
ra is the radius of curvature of an image-side surface of the doublet 11 of the first positive lens group 5;
Dk is the distance between the center axes X1 and Y1 of the individual extreme-object-side lenses of the second positive lens group 6;
D01 is the distance between entrance pupil surfaces; and f1n is the focal distance of the first positive lens group 5.

The amount of change $\Delta Y$ of the image height based on an maximum movement amount $\Delta D$ of the meniscus lens 9 satisfies the following relational expression:

$$\Delta Y = \Delta D \times (Dk/2)/fm.$$

Thus, condition (1) is derived by setting a condition that the amount of change $\Delta Y$ of the image height be less than 20% of the image height ih, that is, $$\Delta Y < ih \times 0.2.$$

The operation of the thus-configured image-acquisition apparatus 1 according to this embodiment will be described below.

With the image-acquisition apparatus 1 according to this embodiment, when the light coming from the object enters the image-acquisition apparatus 1, two images having parallax therebetween are formed in the imaging optical system 2, and the two parallax images are acquired by the image-acquisition device 3. With the light coming from the object, it is possible to ensure a satisfactory angle of view by using the first negative lens group 4, and the diameter of the light bundle focused by the first negative lens group 4 is maintained at a small size by the first positive lens group 5 in the subsequent stage thereof. Then, the light that has passed through the first positive lens group 5 enters the second positive lens group 6, which is provided with the two positive lens groups 12 and 13 that are disposed next to each other in the parallax direction on either side of the common center axis S of the first negative lens group 4 and the first positive lens group 5, and thus, the two parallax images are separated and individually acquired by the image-acquisition device 3.

Because the single meniscus lens 9 provided in the first positive lens group 5 is moved along the common center axis S, it is possible to adjust the focal position by using a simple moving mechanism. By doing so, it is possible to reduce the diameter and the length of the image-acquisition apparatus 1. In other words, with the image-acquisition apparatus 1 according to this embodiment, there is an advantage in that it is possible to prevent an increase in size by simplifying the structure thereof and to sufficiently increase the angle of view.

In addition, it is possible to acquire parallax images having small entrance pupil distances (baseline lengths). Therefore, during stereoscopic observation, it is possible to prevent the parallax of the parallax images that are individually observed by the two eyes, that is, the left and right eyes, from becoming excessively large. By doing so, there is an advantage in that it is possible to reduce fatigue experienced by an operator during stereoscopic observation by facilitating image fusion.

In addition, because the second positive lens group 6 is formed of the meniscus lenses (lens groups) 14 having negative refractive powers, the positive meniscus lenses 15 having positive refractive powers, and the doublets (lens groups) 16 that are sequentially disposed from the object side to the image side, it is possible to focus, at a wide angle, the light bundle emitted from the first positive lens group 5 by using the lens groups 14 having the negative refractive powers, and thus, it is possible to easily correct aberrations in an optical system having a large angle of view.

In addition, in the second positive lens group 6, because the aperture stops 17 are individually disposed between the meniscus lenses (lens groups) 15 having the positive refractive powers and the doublets 16 having the positive refractive powers, it is possible to moderately reduce the entrance pupil distance (baseline length) via the openings of the individual aperture stops 17, and thus, it is possible to facilitate correction of aberrations.

Note that, although the aperture stops are eccentrically disposed on the outer sides of the center axes X2 and Y2 of the individual doublets 16 of the two positive lens groups 12 and 13 of the second positive lens group 6, the aperture stops may be eccentrically disposed with respect to the center axes X1 and Y1 of the object-side lenses 14. By doing so, there is an advantage in that, even if the entrance pupil positions are kept close, it is possible, by displacing the positions at which the parallax images are formed, to achieve a size reduction by reducing the distance between the image-acquisition surfaces or to reduce vignetting of the light bundle by, in contrast, increasing the distance between the image-acquisition surfaces.

In addition, the distance between the centers of the openings of the two aperture stops 17 may be set to be greater than the distance between the center axes X1 and Y1 of the extreme-object-side lenses 14 of the two positive lens groups 12 and 13 in the second positive lens group 6. By doing so, it is possible to reduce crosstalk of the parallax images when the image-acquisition angle of view is increased.

In addition, the distance between the centers of the openings of the two aperture stops 17 may be set to be smaller than the distance between the center axes X1 and Y1 of the extreme-object-side lenses 14 of the two positive lens groups 12 and 13 in the second positive lens group 6. By doing so, it is possible to reduce the size of the image-acquisition surface 18 of the image-acquisition device 3 by reducing the spacing between the parallax images.

In addition, because the first negative lens group 4 is formed of the plano-concave lens 7 provided with the concave surface on the image side and the single meniscus lens 8 having the concave surface on the object side, it is possible to ensure a satisfactory angle of view and to achieve a size reduction. Alternatively, the meniscus lens 8 may be formed of a positive lens component having a positive refractive power. By doing so, it is possible to facilitate ensuring a satisfactory angle of view and correcting aberrations.

In addition, with the image-acquisition apparatus 1 according to this embodiment, because condition (1) is satisfied, it is possible to reduce displacement of the parallax images with respect to each other associated with movement of the meniscus lens 9. By doing so, it is possible to reduce fatigue experienced by the operator during stereoscopic observation by facilitating image fusion when the focal position is changed. In addition, it is possible to reduce aberration fluctuations when focusing.

In addition, with the image-acquisition apparatus 1 according to this embodiment, because condition (2) is satisfied, it is possible to move the image surface without moving the meniscus lens 9 by a large amount. By avoiding a situation in which the upper limit in condition (2) is exceeded, it is possible to achieve a size reduction by reducing the movement amount during focusing by ensuring a satisfactory refractive power of the meniscus lens 9.

In addition, with the image-acquisition apparatus 1 according to this embodiment, because condition (3) is satisfied, by setting the refractive power of the second positive lens group 6 to be moderate so as to avoid a situation in which the lower limit in condition (3) is not reached and so as to avoid a situation in which the upper limit is exceeded, it is possible to employ a configuration that facilitates suppressing aberrations due to eccentricity between a combined optical system formed of the first negative lens group 4 and the first positive lens group 5, which serves as a common lens group, and the second positive lens group 6 with respect to each other.

In other words, if the ratio in condition (3) falls below the lower limit, the refractive power of the second positive lens group 6 becomes relatively low, the refractive power of the common lens group becomes high, and thus, a large aberration due to the eccentricity occurs, making correction thereof difficult. On the other hand, if the ratio in condition (3) exceeds the upper limit, the negative refractive power of the common lens group is increased, which makes it difficult to perform aberration correction in the subsequent stage.

In addition, with the image-acquisition apparatus 1 according to this embodiment, because condition (4) is satisfied, by increasing the radius of curvature by avoiding a situation in which the lower limit is not reached, it is possible to reduce chromatic aberrations due to eccentricity. In addition, ensuring a moderate curvature by avoiding a situation in which the upper limit is exceeded facilitates reducing the radial-direction size of the optical system.

In addition, with the image-acquisition apparatus 1 according to this embodiment, because condition (5) is satisfied, applications to apparatuses that require a large angle of view, such as endoscopes, are possible.

In addition, with the image-acquisition apparatus 1 according to this embodiment, because condition (6) is satisfied, parallax is prevented from becoming excessively large, thus facilitating stereoscopic observation.

Here, an example of the image-acquisition apparatus 1 according to this embodiment will be described below by using FIGS. 3 to 7 and lens data.

FIG. 3 shows the lens arrangement of the imaging optical system 2 of the image-acquisition apparatus 1 according to this example. In addition, FIGS. 4 to 7 show aberration diagrams corresponding to the individual light beams L1 to L7 in the imaging optical system 2 of this example.

In this example, the maximum angle of view (far point) is 126°, the focal distance (far point) is 0.447, the image height is 0.4 mm, and the F-number is 3.5.

In the following lens data, r is the radius of curvature (mm), d is the surface interval (mm), Nd is the refractive index for the d-line, and ν is the Abbe number. In addition, OBJ is the imaging subject (object).

| surface number | r | d | Nd | ν |
|---|---|---|---|---|
| OBJ | ∞ | 18 | | |
| 1 | ∞ | 0.4 | 1.63265 | 57.9917 |
| 2 | 1.50515 | 1.34349 | | |
| 3 | −2.61624 | 1.17382 | 1.74482 | 42.7981 |
| 4 | −3.08491 | 0.285601 | | |
| 5 | −2.63066 | 0.908953 | 1.74256 | 44.9595 |
| 6 | −2.55327 | 0.923544 | | |
| 7 | −2.50621 | 0.816 | 1.48749 | 70.4047 |
| 8 | 3.5032 | 0.263045 | | |
| 9 | 4.27453 | 0.97815 | 1.76182 | 26.5174 |
| 10 | 2.94505 | 1.37011 | 1.64735 | 55.5233 |
| 11 | −4.222020 | | | |
| 12 | ∞ (imaginary surface) | 0.248159 | | |
| 13 | −1.59905 | 0.448159 | 1.48749 | 70.4047 |
| 14 | −2.33316 | 0.4 | | |
| 15 | 3.12084 | 0.5 | 1.7552 | 27.579 |
| 16 | 15.3448 | 0.1 | | |
| 17 | ∞ (aperture) | 0 | | |
| 18 | ∞ (imaginary surface) | 0.1 | | |
| 19 | 1.5844 | 0.4 | 1.92286 | 18.8966 |
| 20 | 0.8 | 0.545631 | 1.589136 | 1.1341 |
| 21 | −3.92172 | 0.99262 | | |
| 22 | ∞ | 0.85 | 1.51633 | 64.1411 |
| 23 | ∞ (imaginary surface) | 0 | | |
| 24 | ∞ (image-acquisition surface) | | | |

The object point, the surface interval 4, and the surface interval 6 in the above-described lens data are values for the case in which the meniscus lens 9 is placed at the far-point position, and the values for the case in which the meniscus lens 9 is placed at the near-point position are:
dOBJ (distance from the object surface to the first surface) =5 mm; d4=1.05914 mm; and d6=0.150005 mm.

In addition, the twelfth surface and the eighteenth surface are imaginary surfaces included in order to indicate eccentricities of the center axes (Y1 and Y2) of the second positive lens group 6; the twenty-third surface is an image surface; and eccentricity amounts yde with respect to the center axes immediately before the object side are:
at the twelfth surface, yde=−0.69174 mm;
at the eighteenth surface, yde=0.05 mm; and,
at the twenty-third surface, yde=−0.02567 mm, respectively.

Next, an image-acquisition apparatus 20 according to a second embodiment of the present invention will be described below with reference to the drawings.

In describing this embodiment, the same reference signs are assigned to portions that have configurations in common with those of the image-acquisition apparatus 1 according to the above-described first embodiment, and descriptions thereof will be omitted.

As shown in FIGS. 8 and 9, an image-acquisition apparatus 20 according to this embodiment differs from the image-acquisition apparatus 1 according to the first embodiment in terms of the configurations of a first negative lens group 22 and a first positive lens group 23 of an imaging optical system 21.

The first negative lens group 22 is provided with, sequentially from the object side: the plano-concave lens (lens component having a negative refractive power) 7 provided with the concave surface on the image side; a biconcave lens 24; and a biconvex lens 25.

In addition, the first positive lens group 23 is provided with, sequentially from the object side: the single meniscus lens (moving lens group) 9 having the concave surface on the object side; and a doublet 26 that is formed of a biconcave lens having a concave surface on the object side and a biconvex lens.

With the image-acquisition apparatus 20 according to this embodiment, because the first negative lens group 22 is formed of the plano-concave lens 7 provided with the concave surface on the image side, the biconcave lens 24, and the biconvex lens (positive lens component) 25 having a positive refractive power, it is possible to facilitate ensuring a satisfactory angle of view and correction of aberrations.

In addition, the second positive lens group 27 of the imaging optical system 21 according to this embodiment is provided with the two positive lens groups 12 and 13 that are disposed on either side of the common center axis S so as to have spaces on both sides thereof and that individually have the center axes X and Y. Each of the positive lens groups 12 and 13 is provided with: the negative meniscus lens 14 having the concave surface on the object side; the positive meniscus lens 28 having the concave surface on the object side; the doublet 16 that is formed of the meniscus lens having the convex surface on the object side and the biconvex lens; and the aperture stop 17 that has an opening, which is eccentrically disposed further toward the outer side than the center axes X and Y, and that is disposed between the positive meniscus lens 28 and the doublet 16.

Here, an example of the image-acquisition apparatus 20 according to this embodiment will be described below by using FIGS. 10 to 14 and lens data.

FIG. 10 shows the lens arrangement of the imaging optical system 21 of the image-acquisition apparatus 20 according to this example. In addition, FIGS. 11 to 14 show aberration diagrams corresponding to the individual light beams L1 to L7 in the imaging optical system 21 of this example.

In this example, the maximum angle of view (far point) is 130°, the focal distance (far point) is 0.492, the image height is 0.4 mm, and the F-number is 3.5.

| surface number | r | d | Nd | ν |
|---|---|---|---|---|
| OBJ | ∞ | 16 | | |
| 1 | ∞ | 0.4 | 1.58866 | 62.0814 |
| 2 | 2.01713 | 1.26438 | | |
| 3 | −3.6754 | 1.12299 | 1.6516 | 58.5498 |
| 4 | 5.3895 | 0.607067 | | |
| 5 | 5.85923 | 0.902268 | 1.7269 | 40.2592 |
| 6 | −5.7411 | 3.24553 | | |
| 7 | −2.62954 | 0.571107 | 1.72 | 50.2298 |
| 8 | −3.52953 | 0.1 | | |
| 9 | −8.39925 | 0.959932 | 1.64771 | 42.6144 |
| 10 | 1.96304 | 1.28656 | 1.63854 | 55.3792 |
| 11 | −4.60278 | 0 | | |
| 12 | ∞ (imaginary surface) | 0.400404 | | |
| 13 | −1.39988 | 0.600404 | 1.744 | 44.7857 |
| 14 | −2.11725 | 0.4 | | |
| 15 | −4.65582 | 0.5 | 1.75435 | 28.1623 |
| 16 | −2.68959 | 0.1 | | |
| 17 | ∞ (aperture) | 0 | | |
| 18 | ∞ (imaginary surface) | 0.1 | | |
| 19 | 1.38124 | 0.4 | 1.92286 | 18.8966 |
| 20 | 0.8 | 0.697876 | 1.58913 | 61.1341 |
| 21 | −16.4714 | 1.29711 | | |
| 22 | ∞ | 0.85 | 1.51633 | 64.1411 |
| 23 | ∞ (imaginary surface) | 0 | | |
| 24 | ∞ (image-acquisition surface) | | | |

The object point, the surface interval 6, and the surface interval 8 in the above-described lens data are values for the case in which the meniscus lens 9 is placed at the far-point position, and the values for the case in which the meniscus lens 9 is placed at the near-point position are:
dOBJ (distance from the object surface to the first surface)= 4 mm; d6=1.92651 mm; and d8=1.41902 mm.

In addition, the twelfth and eighteenth surfaces are imaginary surfaces included in order to indicate eccentricities of the center axis Y of the second positive lens group 27 and the aperture stop 17; the seventeenth surface is the aperture stop 17; the twenty-second surface is an image surface; and eccentricity amounts yde with respect to the center axes immediately before the object side are:
at the twelfth surface, yde=−0.7 mm;
at the seventeenth surface, yde=−0.05 mm;
at the eighteenth surface, yde=0.05 mm; and,
at the twenty-third surface, yde=−0.05725 mm, respectively.

Next, an image-acquisition apparatus 30 according to a third embodiment of the present invention will be described below with reference to the drawings.

In describing this embodiment, the same reference signs are assigned to portions that have configurations in common with those of the image-acquisition apparatus 1 according to the above-described first embodiment, and descriptions thereof will be omitted.

As shown in FIGS. 15 and 16, an image-acquisition apparatus 30 according to this embodiment differs from the image-acquisition apparatus 1 according to the first embodiment in terms of the configurations of a first positive lens group 32 and a second positive lens group 33 of an imaging optical system 31.

In addition, the first positive lens group 32 is provided with, sequentially from the object side: a biconcave lens 34; a meniscus lens 35 having a concave surface on the object side; and a moving lens group having a doublet 36 that is formed of a meniscus lens having a convex surface on the object side and a biconvex lens.

The second positive lens group 33 is provided with, sequentially from the object side: the negative meniscus lenses 14 having the concave surfaces on the object side; meniscus lenses 37 having convex surfaces on the object side; biconvex lenses 38; and the aperture stops 17 provided between the negative meniscus lenses 14 and the meniscus lenses 37.

Here, an example of the image-acquisition apparatus 30 according to this embodiment will be described below by using FIGS. 17 to 21 and lens data.

FIG. 17 shows the lens arrangement of the imaging optical system 31 of the image-acquisition apparatus 30 according to this example. In addition, FIGS. 18 to 21 show aberration diagrams corresponding to the individual light beams L1 to L7 in the imaging optical system 31 of this example.

In this example, the maximum angle of view (far point) is 130°, the focal distance (far point) is 0.461, the image height is 0.4 mm, and the F-number is 3.5.

surface number r d Nd v

| surface number | r | d | Nd | v |
|---|---|---|---|---|
| OBJ | ∞ | 14.0 | | |
| 1 | ∞ | 0.4 | 1.62041 | 60.3227 |
| 2 | 1.74912 | 1.21081 | | |
| 3 | −5.97642 | 1.06942 | 1.92286 | 18.8966 |
| 4 | −3.39832 | 0.553496 | | |
| 5 | −6.26141 | 0.848696 | 1.51633 | 64.1411 |
| 6 | 1.57833 | 0.436056 | | |
| 7 | −2.42926 | 0.68 | 1.6968 | 55.5314 |
| 8 | −3.26785 | 0.252086 | | |
| 9 | 6.01847 | 0.906361 | 1.84666 | 23.7775 |
| 10 | 2.01001 | 1.23299 | 1.66431 | 49.0461 |
| 11 | −2.40937 | 0.176602 | | |
| 12 | ∞ (imaginary surface) | 0.25 | | |
| 13 | −0.917881 | 0.437624 | 1.48749 | 70.2353 |
| 14 | −1.19867 | 0.01 | | |
| 15 | ∞ (aperture) | 0.04 | | |
| 16 | 1.735 | 0.497624 | 1.7552 | 27.579 |
| 17 | 0.78 | 0.12 | | |
| 18 | 1.05684 | 0.60322 | 1.56883 | 56.363 |
| 19 | −1.25682 | 1.23525 | | |
| 20 | ∞ | 0.85 | 1.51633 | 64.1411 |
| 21 | ∞ (imaginary surface) | 0 | | |
| 22 | ∞ (image-acquisition surface) | | | |

The object point, the surface interval 8, and the surface interval 11 in the above-described lens data are values for the case in which the moving lens group 36 is placed at the far-point position, and the values for the case in which the moving lens group 36 is placed at the near-point position are: dOBJ (distance from the object surface to the first surface)=2.5 mm; d8=0.408688 mm; and d11=0.02 mm.

In addition, the twelfth surface is an imaginary surface included in order to indicate the eccentricity of the center axis Y of the second positive lens group 33, and the eccentricity amount yde is:
at the twelfth surface, yde=−0.5 mm.

The values for conditions (1) to (6) for the above-described three examples are shown in Table 1.

According to Table 1, all three examples satisfy conditions (1) to (6).

TABLE 1

| CALCULATION EXPRESSION | | EXAMPLE 1 | EXAMPLE 2 | EXAMPLE 3 |
|---|---|---|---|---|
| fm > (Dk × ΔD)/(ih × 0.4) | fm | 19.46 | 19.50 | 3.32 |
| | (Dk × ΔD)/(ih × 0.4) | 3.34 | 5.77 | 0.49 |
| fm/f1n1p < 10 | fm | 19.46 | 19.50 | 3.32 |
| | f1n1p × 10 | 625.70 | 32.66 | 31.51 |
| 0.1 < fa/f2p < 0.4 | fa/f2p | 0.22 | 0.24 | 0.24 |
| 2 < |ra/Dk| < 20 | ra/Dk | 6.10 | 6.58 | 4.82 |
| ANGLE OF VIEW IS EQUAL TO OR GREATER THAN 100° | | 126.0 | 130.00 | 130.00 |
| 0.2 < D01 < 2 | D01 | 0.69 | 0.70 | 0.50 |

In conditional (1), it is additionally preferable to satisfy:

$$fm > 3*(Dk \times \Delta D)/(ih \times 0.4). \tag{1'}$$

It is more preferable that the upper limit of conditional (2) be 7.

It is more preferable that the lower limit of conditional (3) be 0.2.

It is more preferable that the upper limit of conditional (3) be 0.35.

It is more preferable that the lower limit of conditional (4) be 4, and it is even more preferable that the lower limit thereof be 4.7.

It is more preferable that the upper limit of conditional (4) be 10, and it is even more preferable that the upper limit thereof be 8.

It is more preferable that the lower limit of conditional (5) be 125°.

It is more preferable that the lower limit of conditional (6) be 0.4, and it is even more preferable that the lower limit thereof be 0.45.

It is more preferable that the upper limit of conditional (6) be 1.2, and even more preferable that the upper limit thereof be 0.9.

Example applications of the image-acquisition apparatuses 1, 20, and 30 according to the individual embodiments of the present invention will be described below.

FIG. 22 is a diagram showing an example in which the image-acquisition apparatus 1, 20, or 30 according to the individual embodiments is applied to an endoscope. FIG. 22(*a*) is an overall diagram of a rigid endoscope 110, and FIG. 22(*b*) shows the image-acquisition apparatus 1, 20, or 30 according to the individual embodiments attached to a distal end of the rigid endoscope 110.

In addition, FIG. 23 is an overall diagram showing a flexible electronic endoscope 113. The image-acquisition apparatus 1, 20, or 30 according to the individual embodiments, described above, is attached to a distal end of an inserted portion of the flexible electronic endoscope 113, captured images are subjected to image processing to correct distortion therein, and the images are displayed on a display apparatus 114 in a three-dimensional manner.

As shown in FIGS. 22 and 23, by applying the image-acquisition apparatus 1, 20, or 30 according to the individual embodiments to the endoscope 110 or 113, it is possible to perform observation by capturing wide-viewing-angle images in a three-dimensional manner, and it is possible to observe various sites in a three-dimensional manner.

In addition, FIG. 24 is a diagram showing an example in which the image-acquisition apparatus 1, 20, or 30 according to the individual embodiments of the present invention is applied to an automobile 130.

As shown in FIGS. 24(*a*) and (*b*), a plurality of the image-acquisition apparatuses 1, 20, or 30 are attached to various portions of the automobile 130, acquired images are subjected to image processing to correct distortion therein, and the images are simultaneously displayed, in a three-dimensional manner, on a display apparatus (not shown) in the vehicle interior.

From the above-described embodiments and modifications thereof, the following aspects of the invention are derived. An aspect of the present invention is an image-acquisition apparatus including: an imaging optical system that forms two images having a parallax therebetween; and an image-acquisition device that is disposed closer to an image side than the imaging optical system is and that acquires the parallax images, wherein the imaging optical system is provided with, sequentially from an object side to the image side, a first negative lens group having a negative refractive power, a first positive lens group having a positive refractive power, and a second positive lens group having a positive refractive power, wherein the first positive lens group and the first negative lens group are disposed along a common center axis, wherein the second positive lens group is provided with two positive lens groups that are disposed next to each other in a parallax direction on either side of the common center axis so as to correspond to the respective parallax images and that individually have center axes, wherein two aperture stops having openings that are provided closer to the image side than the first positive lens group is and that are disposed next to each other in the parallax direction on either side of the common center axis so as to correspond to the respective parallax images are provided, and wherein, in the case in which only lenses in which two surfaces thereof, that is, an object-side surface and an image-side surface thereof, on the center axes are in contact with air serve as lens components, the first negative lens group is provided with a lens component having a negative refractive power on the extreme object side, the first positive lens group includes only one moving lens group that is moved along the common center axis when focusing, all of remaining lens components in the imaging optical system, excluding the moving lens group, remain still, and the moving lens group satisfies condition (1):

$$fm > (Dk \times \Delta D)/(ih \times 0.4), \tag{1}$$

where fm is an absolute value of a focal distance of the moving lens group, $\Delta D$ is a maximum movement amount of the moving lens group, ih is an image height of the parallax image, and Dk is a distance between center axes of the individual extreme-object-side lenses of the second positive lens group.

With this aspect, when the light coming from the object enters the image-acquisition apparatus, two images having parallax therebetween are formed in the imaging optical system, and the two parallax images are acquired by the image-acquisition device. With the light coming from the object, it is possible to ensure a satisfactory angle of view by using the first negative lens group, and the diameter of the light bundle focused by the first negative lens group is maintained at a small size by the first positive lens group in the subsequent stage thereof. Then, the light that has passed through the first positive lens group enters the second positive lens group, which is provided with the two positive lens groups that are disposed next to each other in the parallax direction on either side of the common center axis of the first negative lens group and the first positive lens group, and thus, the two parallax images are separated and individually acquired by the image-acquisition device.

By moving only one of the moving lens groups provided in the first positive lens group along the common center axis, it is possible to adjust the focal position by using a single moving mechanism. By doing so, it is possible to reduce the diameter and the length of the image-acquisition apparatus. In other words, with this aspect, it is possible to prevent an increase in the size by simplifying the structure and to sufficiently increase the angle of view. In addition, it is possible to acquire parallax images having a small entrance pupil distance (baseline length).

It is possible to reduce displacement of the parallax images with respect to each other associated with movement of the moving lens group. By doing so, it is possible to reduce fatigue experienced by the operator during stereoscopic observation by facilitating image fusion when the focal position is changed. In addition, it is possible to reduce aberration fluctuations when focusing.

In the above-described aspect, the moving lens group may satisfy the following condition (2):

$$fm/f1n1p<10, \qquad (2)$$

where fm is an absolute value of a focal distance of the moving lens group, and f1n1p is an absolute value of a combined focal distance of the first negative lens group and the first positive lens group when focusing on a far object.

By doing so, it is possible to move the image surface without moving the moving lens group by a large amount. By avoiding a situation in which the upper limit is exceeded in condition (2), it is possible to achieve size reduction by reducing the movement amount during focusing by ensuring a satisfactory refractive power of the moving lens group.

In the above-described aspect, each of the positive lens groups of the second positive lens group may be formed of a lens group having a negative refractive power and a lens group having a positive refractive power that are sequentially disposed from the object side to the image side.

By doing so, it is possible to expand the light bundle emitted from the second positive lens group by means of the lens group having the negative refractive power, and aberration correction is also facilitated in an optical system having a large angle of view.

In the above-described aspect, each of the aperture stops may be disposed between the lens group having the negative refractive power and the lens group having the positive refractive power in the second positive lens group.

By doing so, it is possible to moderately reduce the entrance pupil distance (baseline length) via the openings of the individual aperture stops, and thus, it is possible to facilitate correcting aberrations.

Another aspect of the present invention is an image-acquisition apparatus including: an imaging optical system that forms two images having a parallax therebetween; and an image-acquisition device that is disposed closer to an image side than the imaging optical system is and that acquires the parallax images, wherein the imaging optical system is provided with, sequentially from an object side to the image side, a first negative lens group having a negative refractive power, a first positive lens group having a positive refractive power, and a second positive lens group having a positive refractive power, wherein the first positive lens group and the first negative lens group are disposed along a common center axis, wherein the second positive lens group is provided with two positive lens groups that are disposed next to each other in a parallax direction on either side of the common center axis so as to correspond to the respective parallax images and that individually have center axes, wherein two aperture stops having openings that are provided closer to the image side than the first positive lens group is and that are disposed next to each other in the parallax direction on either side of the common center axis so as to correspond to the respective parallax images are provided, and wherein, in the case in which only lenses in which two surfaces thereof, that is, an object-side surface and an image-side surface thereof, on the center axes are in contact with air serve as lens components, the first negative lens group is provided with a lens component having a negative refractive power on the extreme object side, the first positive lens group includes only one moving lens group that is moved along the common center axis when focusing, all of remaining lens components in the imaging optical system, excluding the moving lens group, remain still, and a center of the opening of at least one of the aperture stops may be eccentrically disposed with respect to the center axis of the positive lens group that is in the same parallax direction as the opening relative to the common center axis.

By doing so, even if the entrance pupil positions are kept close, it is possible, by displacing the positions at which the parallax images are formed, to reduce vignetting of the light bundle.

In the above-described aspect, a distance between the centers of the two openings may be greater than a distance between the center axes of the extreme-object-side lenses of the two positive lens groups in the second positive lens group.

By doing so, it is possible to reduce crosstalk of the parallax images when the image-acquisition angle of view is increased.

In the above-described aspect, a distance between the centers of the two openings may be smaller than a distance between the center axes of the extreme-object-side lenses of the two positive lens groups in the second positive lens group.

By doing so, it is possible to reduce the size of the image-acquisition surface of the image-acquisition device by reducing the spacing between the parallax images.

Another aspect of the present invention is an image-acquisition apparatus including: an imaging optical system that forms two images having a parallax therebetween; and an image-acquisition device that is disposed closer to an image side than the imaging optical system is and that acquires the parallax images, wherein the imaging optical system is provided with, sequentially from an object side to the image side, a first negative lens group having a negative refractive power, a first positive lens group having a positive refractive power, and a second positive lens group having a positive refractive power, wherein the first positive lens group and the first negative lens group are disposed along a common center axis, wherein the second positive lens group is provided with two positive lens groups that are disposed next to each other in a parallax direction on either side of the common center axis so as to correspond to the respective parallax images and that individually have center axes, wherein two aperture stops having openings that are provided closer to the image side than the first positive lens group is and that are disposed next to each other in the parallax direction on either side of the common center axis so as to correspond to the respective parallax images are provided, and wherein, in the case in which only lenses in which two surfaces thereof, that is, an object-side surface and an image-side surface thereof, on the center axes are in contact with air serve as lens components, the first negative lens group is provided with a lens component having a negative refractive power on the extreme object side, the first positive lens group includes only one moving lens group that is moved along the common center axis when focusing, all of remaining lens components in the imaging optical system, excluding the moving lens group, remain still, and the first negative lens group may be formed of two lens components including the lens component having the negative refractive power.

By doing so, by constituting the first negative lens group by using the two negative lens components, it is possible to ensure a satisfactory angle of view and to achieve a size reduction. On the other hand, by constituting the first negative lens group by using the negative lens component and the positive lens component, it is possible to facilitate ensuring a satisfactory angle of view and correction of aberrations.

Another aspect of the present invention is an image-acquisition apparatus including: an imaging optical system that forms two images having a parallax therebetween; and an image-acquisition device that is disposed closer to an image side than the imaging optical system is and that acquires the parallax images, wherein the imaging optical system is provided with, sequentially from an object side to the image side, a first negative lens group having a negative refractive power, a first positive lens group having a positive refractive power, and a second positive lens group having a positive refractive power, wherein the first positive lens group and the first negative lens group are disposed along a common center axis, wherein the second positive lens group is provided with two positive lens groups that are disposed next to each other in a parallax direction on either side of the common center axis so as to correspond to the respective parallax images and that individually have center axes, wherein two aperture stops having openings that are provided closer to the image side than the first positive lens group is and that are disposed next to each other in the parallax direction on either side of the common center axis so as to correspond to the respective parallax images are provided, and wherein, in the case in which only lenses in which two surfaces thereof, that is, an object-side surface and an image-side surface thereof, on the center axes are in contact with air serve as lens components, the first negative lens group is provided with a lens component having a negative refractive power on the extreme object side, the first positive lens group includes only one moving lens group that is moved along the common center axis when focusing, all of remaining lens components in the imaging optical system, excluding the moving lens group, remain still, and the second positive lens group may satisfy the following condition (3):

$$0.1 < fa/f2p < 0.4, \tag{3}$$

where fa is a focal distance when focusing on a far object by arranging, on a straight line, the individual center axes of the first negative lens group, the first positive lens group, and the second positive lens group by moving the second positive lens group in a direction substantially orthogonal to the common center axis of the first negative lens group and the first positive lens group, and f2p is a focal distance of the second positive lens group.

By setting the refractive power of the second positive lens group to be moderate so as to avoid a situation in which the lower limit in condition (3) is not reached and so as to avoid a situation in which the upper limit is exceeded, it is possible to employ a configuration that facilitates suppressing aberrations due to eccentricity between a combined optical system formed of the first negative lens group and the first positive lens group, which serves as a common lens group, and the optical system of the second positive lens group with respect to each other.

In other words, if the ratio in condition (3) falls below the lower limit, the refractive power of the second positive lens group becomes relatively low, the refractive power of the common lens group becomes high, and thus, a large aberration due to the eccentricity occurs, making correction thereof difficult. On the other hand, if the ratio in condition (3) exceeds the upper limit, the negative refractive power of the common lens group is increased, which makes it difficult to perform aberration correction in the subsequent stage.

In the above-described aspect, the first positive lens group may be provided with a doublet component that is disposed on an extreme image side in the first positive lens group, in which a convex surface thereof faces the image side, and that includes a positive lens and a negative lens, and the following condition (4) may be satisfied:

$$2 < |ra/Dk| < 20, \tag{4}$$

where ra is a radius of curvature of an image-side surface of the doublet component, and Dk is a distance between center axes of the individual extreme-object-side lenses of the second positive lens group.

The condition (4) specifies the curvature of the extreme-image-side refractive surface of the first positive lens group. By increasing the radius of curvature by avoiding a situation in which the lower limit is not reached in condition (4), it is possible to reduce chromatic aberrations due to eccentricity. In addition, ensuring a moderate curvature by avoiding a situation in which the upper limit is exceeded in condition (4) facilitates reducing the radial-direction size of the optical system.

In the above-described aspect, the moving lens group in the first positive lens group may be provided with a doublet component including a positive lens and a negative lens.

By doing so, it is possible to reduce chromatic aberrations.

Another aspect of the present invention is an image-acquisition apparatus including: an imaging optical system that forms two images having a parallax therebetween; and an image-acquisition device that is disposed closer to an image side than the imaging optical system is and that acquires the parallax images, wherein the imaging optical system is provided with, sequentially from an object side to the image side, a first negative lens group having a negative refractive power, a first positive lens group having a positive refractive power, and a second positive lens group having a positive refractive power, wherein the first positive lens group and the first negative lens group are disposed along a common center axis, wherein the second positive lens group is provided with two positive lens groups that are disposed next to each other in a parallax direction on either side of the common center axis so as to correspond to the respective parallax images and that individually have center axes, wherein two aperture stops having openings that are provided closer to the image side than the first positive lens group is and that are disposed next to each other in the parallax direction on either side of the common center axis so as to correspond to the respective parallax images are provided, and wherein, in the case in which only lenses in which two surfaces thereof, that is, an object-side surface and an image-side surface thereof, on the center axes are in contact with air serve as lens components, the first negative lens group is provided with a lens component having a negative refractive power on the extreme object side, the first positive lens group includes only one moving lens group that is moved along the common center axis when focusing, all of remaining lens components in the imaging optical system, excluding the moving lens group, remain still, the first positive lens group may be formed of two positive lens component and one negative lens component, and the moving lens group may be any one of the positive lens components of the first positive lens group.

By doing so, it is possible to achieve both a size reduction and aberration correction.

In the above-described aspect, it is preferable that condition (5) be satisfied:

a maximum angle of view is equal to or greater than 100° when focusing on a far object. (5)

In the above-described aspect, it is preferable that condition (6) be satisfied:

$$0.2 < D01 < 2, \tag{6}$$

where D01 is a distance between entrance pupil surfaces.

REFERENCE SIGNS LIST 1, 20, 30 image-acquisition apparatus
2, 21, 31 imaging optical system
3 image-acquisition device
4, 22 first negative lens group
5, 23, 32 first positive lens group
6, 27, 33 second positive lens group
9 meniscus lens (moving lens group)
12, 13 positive lens group
17 aperture stop
36 doublet (moving lens group)
S, X, Y, X1, X2, Y1, Y2 center axis

TABLE 1

| CALCULATION EXPRESSION | | EXAMPLE 1 | EXAMPLE 2 | EXAMPLE 3 |
|---|---|---|---|---|
| $fm > (Dk \times \Delta D)/(ih \times 0.4)$ | fm | 19.46 | 19.50 | 3.32 |
| | $(Dk \times \Delta D)/(ih \times 0.4)$ | 3.34 | 5.77 | 0.49 |
| $fm/f1n1p < 10$ | fm | 19.46 | 19.50 | 3.32 |
| | $f1n1p \times 10$ | 625.70 | 32.66 | 31.51 |
| $0.1 < fa/f2p < 0.4$ | $fa/f2p$ | 0.22 | 0.24 | 0.24 |
| $2 < |ra/Dk| < 20$ | $ra/Dk$ | 6.10 | 6.58 | 4.82 |
| ANGLE OF VIEW IS EQUAL TO OR GREATER THAN 100° | | 126.0 | 130.00 | 130.00 |
| $0.2 < D01 < 2$ | D01 | 0.69 | 0.70 | 0.50 |

The invention claimed is:

1. An image-acquisition apparatus comprising:
an imaging optical system that forms two images having parallax therebetween; and
an image-acquisition device that is disposed closer to an image side than the imaging optical system is and that acquires the parallax images,
wherein the imaging optical system is provided with, sequentially from an object side to the image side, a first negative lens group having a negative refractive power, a first positive lens group having a positive refractive power, and a second positive lens group having a positive refractive power,
wherein the first positive lens group and the first negative lens group are disposed along a common center axis,
wherein the second positive lens group is provided with two positive lens groups that are disposed next to each other in a parallax direction on either side of the common center axis so as to correspond to the respective parallax images and that individually have center axes,
wherein two aperture stops having openings that are provided closer to the image side than the first positive lens group is and that are disposed next to each other in the parallax direction on either side of the common center axis so as to correspond to the respective parallax images are provided, and
wherein a lens component is defined as a lens in which both an object-side surface of the lens and an image side surface of the lens are in contact with air along a center axis of the lens,
wherein the first negative lens group is provided with a lens component having a negative refractive power on the extreme object side,
wherein the first positive lens group includes only one moving lens group that is moved along the common center axis when focusing,
wherein all of remaining lens components in the imaging optical system, excluding the moving lens group, remain still, and
wherein condition (5) is satisfied:
(5) a maximum angle of view is equal to or greater than 100° when focusing on a far object.

2. The image-acquisition apparatus according to claim 1, wherein the moving lens group satisfies condition (1):

$$fm > (Dk \times \Delta D)/(ih \times 0.4), \qquad (1)$$

where
fm is an absolute value of a focal distance of the moving lens group,
$\Delta D$ is a maximum movement amount of the moving lens group,
ih is an image height of the parallax image, and
Dk is a distance between center axes of the individual extreme-object-side lenses of the second positive lens group.

3. The image-acquisition apparatus according to claim 2, wherein the moving lens group satisfies condition (2):

$$fm/f1n1p < 10, \qquad (2)$$

where
fm is an absolute value of a focal distance of the moving lens group, and
f1n1p is an absolute value of a combined focal distance of the first negative lens group and the first positive lens group when focusing on a far object.

4. The image-acquisition apparatus according to claim 2, wherein each of the positive lens groups of the second positive lens group is formed of a lens group having a negative refractive power and a lens group having a positive refractive power that are sequentially disposed from the object side to the image side.

5. The image-acquisition apparatus according to claim 4, wherein each of the aperture stops is disposed between the lens group having the negative refractive power and the lens group having the positive refractive power in the second positive lens group.

* * * * *